United States Patent
Dean et al.

(10) Patent No.: US 6,204,055 B1
(45) Date of Patent: Mar. 20, 2001

(54) ANTISENSE INHIBITION OF FAS MEDIATED SIGNALING

(75) Inventors: Nicholas M. Dean, Olivenhain; Eric G. Marcusson, San Diego, both of CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/290,640

(22) Filed: Apr. 12, 1999

(51) Int. Cl.[7] .......................... C07H 21/04; A61K 48/00; C12N 15/85; C12N 15/86
(52) U.S. Cl. .................. 435/375; 435/325; 435/91.1; 536/23.1; 536/24.5; 514/44
(58) Field of Search ............................. 435/6, 91.1, 91.3, 435/325, 375; 536/23.1, 23.2, 24.5, 24.3, 24.31, 24.33; 514/44

(56) References Cited

U.S. PATENT DOCUMENTS 5,912,168 * 6/1999 Watson et al. ..................... 435/320.1

FOREIGN PATENT DOCUMENTS

96/20206 * 7/1996 (WO) .

OTHER PUBLICATIONS

Du et al., "A Hammerhead Ribozyme That Cleaves Perforin and Fas–ligand RNA's in Vitro", Biochem. Biophys. Res. Commun., 1996, 226, 595–600.

Freiss et al., "Extinction of Insulin–Like Growth Factor–I Mitogenic Signaling by Antiestrogen–Stimulated Fas–Associated Protein Tyrosine Phosphatase–1 in Human Breast Cancer Cells", Mol. Endocrinol., 1998, 12, 568–579.

Herr et al., "Activation of CD95 (APO–1/FAS) signaling by ceramide mediates cancer therapy–induced apoptosis", EMBO J., 1997, 16, 6200–6208.

Lee et al., "The Fas System Is a Key Regulator of Germ Cell Apoptosis in the Testis*", Endocrinology, 1997, 138, 2081–2088.

O'Connell et al., "The Fas Counterattack: Fas–mediated T Cell Killing by Colon Cancer Cells Expressing Fas Ligand", J. Exp. Med., 1996, 184, 1075–1082.

Turley et al., "Vitamin E Succinate Induces Fas–mediated Apoptosis in Estrogen Receptor–Negative Human Breast Cancer Cells[1]", Cancer Res., 1997, 57, 881–890.

Yu et al., "Vitamin E Succinate (VES) Induces Fas Sensitivity in Human Breast Cancer Cells:Role for $M_r$ 43,000 Fas in VES–triggered Apoptosis[1]", Cancer Res., 1999, 59, 953–961.

* cited by examiner

Primary Examiner—Robert A. Schwartzman
Assistant Examiner—Karen A Lacourciere
(74) Attorney, Agent, or Firm—Law Offices of Jane Massey Licata

(57) ABSTRACT

Compounds, compositions and methods are provided for inhibiting Fas mediated signaling. The compositions comprise antisense compounds targeted to nucleic acids encoding Fas, FasL and Fap-1. Methods of using these antisense compounds for inhibition of Fas, FasL and Fap-1 expression and for treatment of diseases, particularly autoimmune and inflammatory diseases and cancers, associated with overexpression or constitutive activation of Fas, FasL or Fap-1 are provided.

39 Claims, No Drawings

SEQUENCE LISTING

<160> NUMBER OF SEQ ID NOS: 85

<210> SEQ ID NO 1
<211> LENGTH: 2551
<212> TYPE: DNA
<213> ORGANISM: Homo sapiens
<220> FEATURE:
<221> NAME/KEY: CDS
<222> LOCATION: (221)..(1228)
<300> PUBLICATION INFORMATION:
<303> JOURNAL: J. Biol. Chem.
<304> VOLUME: 267
<305> ISSUE: 15
<306> PAGES: 10709-10715
<307> DATE: 1992-05-25
<308> DATABASE ACCESSION NUMBER: X63717/Genbank
<309> DATABASE ENTRY DATE: 1996-07-19

<400> SEQUENCE: 1

```
gcaagagtga cacacaggtg ttcaaagacg cttctgggga gtgagggaag cggtttacga       60
gtgacttggc tggagcctca ggggcgggca ctggcacgac acacccctg aggccagccc       120 tggctgccca ggcggagctg cctcttctcc cgcgggttgg tggacccgct cagtacggag      180
ttggggaagc tctttcactt cggaggattg ctcaacaacc atg ctg ggc atc tgg       235
                                              Met Leu Gly Ile Trp
                                                1               5 acc ctc cta cct ctg gtt ctt acg tct gtt gct aga tta tcg tcc aaa       283
Thr Leu Leu Pro Leu Val Leu Thr Ser Val Ala Arg Leu Ser Ser Lys
                10                  15                  20 agt gtt aat gcc caa gtg act gac atc aac tcc aag gga ttg gaa ttg       331
Ser Val Asn Ala Gln Val Thr Asp Ile Asn Ser Lys Gly Leu Glu Leu
        25                  30                  35 agg aag act gtt act aca gtt gag act cag aac ttg gaa ggc ctg cat       379
Arg Lys Thr Val Thr Thr Val Glu Thr Gln Asn Leu Glu Gly Leu His
    40                  45                  50 cat gat ggc caa ttc tgc cat aag ccc tgt cct cca ggt gaa agg aaa       427
His Asp Gly Gln Phe Cys His Lys Pro Cys Pro Pro Gly Glu Arg Lys
55                  60                  65 gct agg gac tgc aca gtc aat ggg gat gaa cca gac tgc gtg ccc tgc       475
Ala Arg Asp Cys Thr Val Asn Gly Asp Glu Pro Asp Cys Val Pro Cys
70                  75                  80                  85 caa gaa ggg aag gag tac aca gac aaa gcc cat ttt tct tcc aaa tgc       523
Gln Glu Gly Lys Glu Tyr Thr Asp Lys Ala His Phe Ser Ser Lys Cys
                90                  95                  100 aga aga tgt aga ttg tgt gat gaa gga cat ggc tta gaa gtg gaa ata       571
Arg Arg Cys Arg Leu Cys Asp Glu Gly His Gly Leu Glu Val Glu Ile
            105                 110                 115 aac tgc acc cgg acc cag aat acc aag tgc aga tgt aaa cca aac ttt       619
Asn Cys Thr Arg Thr Gln Asn Thr Lys Cys Arg Cys Lys Pro Asn Phe
        120                 125                 130 ttt tgt aac tct act gta tgt gaa cac tgt gac cct tgc acc aaa tgt       667
Phe Cys Asn Ser Thr Val Cys Glu His Cys Asp Pro Cys Thr Lys Cys
    135                 140                 145 gaa cat gga atc atc aag gaa tgc aca ctc acc agc aac acc aag tgc       715
Glu His Gly Ile Ile Lys Glu Cys Thr Leu Thr Ser Asn Thr Lys Cys
150                 155                 160                 165 aaa gag gaa gga tcc aga tct aac ttg ggg tgg ctt tgt ctt ctt ctt       763
Lys Glu Glu Gly Ser Arg Ser Asn Leu Gly Trp Leu Cys Leu Leu Leu
                170                 175                 180 ttg cca att cca cta att gtt tgg gtg aag aga aag gaa gta cag aaa       811
Leu Pro Ile Pro Leu Ile Val Trp Val Lys Arg Lys Glu Val Gln Lys
```

|  |  |  |  |  |  |  |  |  |  |  |  |  |  |  |  |
|--|--|--|--|--|--|--|--|--|--|--|--|--|--|--|--|
|  | 185 |  |  |  |  | 190 |  |  |  |  | 195 |  |  |  |  |
| aca | tgc | aga | aag | cac | aga | aag | gaa | aac | caa | ggt | tct | cat | gaa | tct | cca |
| Thr | Cys | Arg | Lys | His | Arg | Lys | Glu | Asn | Gln | Gly | Ser | His | Glu | Ser | Pro |
|  |  | 200 |  |  |  |  | 205 |  |  |  |  | 210 |  |  |  |

859 acc tta aat cct gaa aca gtg gca ata aat tta tct gat gtt gac ttg    907
Thr Leu Asn Pro Glu Thr Val Ala Ile Asn Leu Ser Asp Val Asp Leu
        215                 220                 225 agt aaa tat atc acc act att gct gga gtc atg aca cta agt caa gtt    955
Ser Lys Tyr Ile Thr Thr Ile Ala Gly Val Met Thr Leu Ser Gln Val
230                 235                 240                 245 aaa ggc ttt gtt cga aag aat ggt gtc aat gaa gcc aaa ata gat gag   1003
Lys Gly Phe Val Arg Lys Asn Gly Val Asn Glu Ala Lys Ile Asp Glu
            250                 255                 260 atc aag aat gac aat gtc caa gac aca gca gaa cag aaa gtt caa ctg   1051
Ile Lys Asn Asp Asn Val Gln Asp Thr Ala Glu Gln Lys Val Gln Leu
                265                 270                 275 ctt cgt aat tgg cat caa ctt cat gga aag aaa gaa gcg tat gac aca   1099
Leu Arg Asn Trp His Gln Leu His Gly Lys Lys Glu Ala Tyr Asp Thr
        280                 285                 290 ttg att aaa gat ctc aaa aaa gcc aat ctt tgt act ctt gca gag aaa   1147
Leu Ile Lys Asp Leu Lys Lys Ala Asn Leu Cys Thr Leu Ala Glu Lys
295                 300                 305 att cag act atc atc ctc aag gac att act agt gac tca gaa aat tca   1195
Ile Gln Thr Ile Ile Leu Lys Asp Ile Thr Ser Asp Ser Glu Asn Ser
310                 315                 320                 325 aac ttc aga aat gaa atc caa agc ttg gtc tag agtgaaaaac aacaaattca  1248
Asn Phe Arg Asn Glu Ile Gln Ser Leu Val
                330                 335 gttctgagta tatgcaatta gtgtttgaaa agattcttaa tagctggctg taaatactgc  1308
ttggttttt actgggtaca ttttatcatt tattagcgct gaagagccaa catatttgta  1368
gatttttaat atctcatgat tctgcctcca aggatgttta aaatctagtt gggaaaacaa  1428
acttcatcaa gagtaaatgc agtggcatgc taagtaccca aataggagtg tatgcagagg  1488
atgaaagatt aagattatgc tctggcatct aacatatgat tctgtagtat gaatgtaatc  1548
agtgtatgtt agtacaaatg tctatccaca ggctaacccc actctatgaa tcaatagaag  1608
aagctatgac cttttgctga aatatcagtt actgaacagg caggccactt tgcctctaaa  1668
ttacctctga taattctaga gattttacca tatttctaaa ctttgtttat aactctgaga  1728
agatcatatt tatgtaaagt atatgtattt gagtgcagaa tttaaataag gctctacctc  1788
aaagaccttt gcacagttta ttggtgtcat attatacaat atttcaattg tgaattcaca  1848
tagaaaacat taaattataa tgtttgacta ttatatatgt gtatgcattt tactggctca  1908
aaactaccta cttctttctc aggcatcaaa agcatttga gcaggagagt attactagag   1968
ctttgccacc tctccatttt tgccttggtg ctcatcttaa tggcctaatg cacccccaaa  2028
catggaaata tcaccaaaaa atacttaata gtccaccaaa aggcaagact gcccttagaa  2088
attctagcct ggtttggaga tactaactgc tctcagagaa agtagctttg tgacatgtca  2148
tgaacccatg tttgcaatca aagatgataa aatagattct tattttccc ccaccccga    2208
aaatgttcaa taatgtccca tgtaaaacct gctacaaatg gcagcttata catagcaatg  2268
gtaaaatcat catctggatt taggaattgc tcttgtcata cccccaagtt tctaagattt  2328
aagattctcc ttactactat cctacgttta aatatctttg aaagtttgta ttaaatgtga  2388
atttttaagaa ataatattta tatttctgta aatgtaaact gtgaagatag ttataaactg  2448
aagcagatac ctggaaccac ctaaagaact tccatttatg gaggatttt ttgcccccttg   2508 tgtttggaat tataaaatat aggtaaaagt acgtaattaa ata                    2551

<210> SEQ ID NO 2
<211> LENGTH: 335
<212> TYPE: PRT
<213> ORGANISM: Homo sapiens

<400> SEQUENCE: 2

Met Leu Gly Ile Trp Thr Leu Pro Leu Val Leu Thr Ser Val Ala
 1               5                  10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Val Glu Thr Gln Asn
            35                  40                  45

Leu Glu Gly Leu His His Asp Gly Gln Phe Cys His Lys Pro Cys Pro
        50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
cgtaaaccgc ttccctcact                                      20

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
gtgttccgtg ccagtgcccg                                      20

<210> SEQ ID NO 5
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 5
gcccagcatg gttgttgagc                                      20

<210> SEQ ID NO 6
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 6
cttcctcaat tccatccct                                       20

<210> SEQ ID NO 7
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 7
cttcttggca gggcacgcag                                      20

<210> SEQ ID NO 8
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 8
tgcacttggt attctgggtc                                      20

<210> SEQ ID NO 9
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 9
gctggtgagt gtgcattcct                                      20

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 10
cattgacacc attctttcga                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
tcactctaga ccaagctttg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 12
cccagtaaaa aaccaagcag                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 13
tatgttggct cttcagcgct                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 14
atttgggtac ttagcatgcc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 15
gggttagcct gtggatagac                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 16
caaagtggcc tgcctgttca                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 17
ttgagccagt aaaatgcata                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 18
tgagcaccaa ggcaaaaatg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 19
tcttgccttt tggtggacta                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 20
agcaggtttt acatgggaca                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 21
ggtatgacaa gagcaattcc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 22
ggtggttcca ggtatctgct                                              20

<210> SEQ ID NO 23
```

-continued

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 23
tataattcca aacacaaggg                                              20

<210> SEQ ID NO 24
<211> LENGTH: 1890
<212> TYPE: DNA
<213> ORGANISM: Homo sapiens
<220> FEATURE:
<221> NAME/KEY: CDS
<222> LOCATION: (189)..(1034)
<300> PUBLICATION INFORMATION:
<303> JOURNAL: Biochim. Biophys. Acta
<304> VOLUME: 204
<305> ISSUE: 2
<306> PAGES: 468-474
<307> DATE: 1994-10-28
<308> DATABASE ACCESSION NUMBER: D31822/Genbank
<309> DATABASE ENTRY DATE: 1999-02-08

<400> SEQUENCE: 24
aaacagagag agatagagaa agagaaagac agaggtgttt cccttagcta tggaaactct    60
ataagagaga tccagcttgc ctcctcttga gcagtcagca acagggtccc gtccttgaca   120
cctcagcctc tacaggactg agaagaagta aaaccgtttg ctggggctgg cctgactcac   180 cagctgcc atg cag cag ccc ttc aat tac cca tat ccc cag atc tac tgg   230
         Met Gln Gln Pro Phe Asn Tyr Pro Tyr Pro Gln Ile Tyr Trp
           1               5                  10 gtg gac agc agt gcc agc tct ccc tgg gcc cct cca ggc aca gtt ctt   278
Val Asp Ser Ser Ala Ser Ser Pro Trp Ala Pro Pro Gly Thr Val Leu
 15                  20                  25                  30 ccc tgt cca acc tct gtg ccc aga agg cct ggt caa agg agg cca cca   326
Pro Cys Pro Thr Ser Val Pro Arg Arg Pro Gly Gln Arg Arg Pro Pro
                 35                  40                  45 cca cca ccg cca ccg cca cca cta cca cct ccg ccg ccg cca cca       374
Pro Pro Pro Pro Pro Pro Leu Pro Pro Pro Pro Pro Pro Pro
             50                  55                  60 ctg cct cca cta ccg ctg cca ccc ctg aag aag aga ggg aac cac agc   422
Leu Pro Pro Leu Pro Leu Pro Pro Leu Lys Lys Arg Gly Asn His Ser
             65                  70                  75 aca ggc ctg tgt ctc ctt gtg atg ttt tct atg gtt ctg gtt gcc ttg   470
Thr Gly Leu Cys Leu Leu Val Met Phe Phe Met Val Leu Val Ala Leu
 80                  85                  90 gta gga ttg ggc ctg ggg atg ttt cag ctc ttc cac cta cag aag gag   518
Val Gly Leu Gly Leu Gly Met Phe Gln Leu Phe His Leu Gln Lys Glu
 95                 100                 105                 110 ctg gca gaa ctc cga gag tct acc agc cag atg cac aca gca tca tct   566
Leu Ala Glu Leu Arg Glu Ser Thr Ser Gln Met His Thr Ala Ser Ser
                115                 120                 125 ttg gag aag caa ata ggc cac ccc agt cca ccc cct gaa aaa aag gag   614
Leu Glu Lys Gln Ile Gly His Pro Ser Pro Pro Pro Glu Lys Lys Glu
            130                 135                 140 ctg agg aaa gtg gcc cat tta aca ggc aag tcc aac tca agg tcc atg   662
Leu Arg Lys Val Ala His Leu Thr Gly Lys Ser Asn Ser Arg Ser Met
        145                 150                 155 cct ctg gaa tgg gaa gac acc tat gga att gtc ctg ctt tct gga gtg   710
Pro Leu Glu Trp Glu Asp Thr Tyr Gly Ile Val Leu Leu Ser Gly Val
    160                 165                 170 aag tat aag aag ggt ggc ctt gtg atc aat gaa act ggg ctg tac ttt   758
Lys Tyr Lys Lys Gly Gly Leu Val Ile Asn Glu Thr Gly Leu Tyr Phe
```

-continued

```
Lys Tyr Lys Lys Gly Gly Leu Val Ile Asn Glu Thr Gly Leu Tyr Phe
175                 180                 185                 190 gta tat tcc aaa gta tac ttc cgg ggt caa tct tgc aac aac ctg ccc      806
Val Tyr Ser Lys Val Tyr Phe Arg Gly Gln Ser Cys Asn Asn Leu Pro
                195                 200                 205 ctg agc cac aag gtc tac atg agg aac tct aag tat ccc cag gat ctg      854
Leu Ser His Lys Val Tyr Met Arg Asn Ser Lys Tyr Pro Gln Asp Leu
            210                 215                 220 gtg atg atg gag ggg aag atg atg agc tac tgc act act ggg cag atg      902
Val Met Met Glu Gly Lys Met Met Ser Tyr Cys Thr Thr Gly Gln Met
        225                 230                 235 tgg gcc cgc agc agc tac ctg ggg gca gtg ttc aat ctt acc agt gct      950
Trp Ala Arg Ser Ser Tyr Leu Gly Ala Val Phe Asn Leu Thr Ser Ala
    240                 245                 250 gat cat tta tat gtc aac gta tct gag ctc tct ctg gtc aat ttt gag      998
Asp His Leu Tyr Val Asn Val Ser Glu Leu Ser Leu Val Asn Phe Glu
255                 260                 265                 270 gaa tct cag acg ttt ttc ggc tta tat aag ctc taa gagaagcact           1044
Glu Ser Gln Thr Phe Phe Gly Leu Tyr Lys Leu
                275                 280 ttgggattct ttccattatg attctttgtt acaggcaccg agaatgttgt attcagtgag    1104
ggtcttctta catgcatttg aggtcaagta agaagacatg aaccaagtgg accttgagac    1164
cacagggttc aaaatgtctg tagctcctca actcacctaa tgtttatgag ccagacaaat    1224
ggaggaatat gacggaagaa catagaactc tgggctgcca tgtgaagagg gagaagcatg    1284
aaaaagcagc tacccaggtg ttctacactc atcttagtgc ctgagagtat ttaggcagat    1344
tgaaaaggac acctttaac tcacctctca aggtgggcct tgctacctca aggggggactg    1404 tctttcagat acatggttgt gacctgagga tttaagggat ggaaaggaa gactagaggc     1464 ttgcataata agctaaagag gctgaaagag gccaatgccc cactggcagc atcttcactt    1524
ctaaatgcat atcctgagcc atcggtgaaa ctaacagata agcaagagag atgtttttggg   1584 gactcatttc attcctaaca cagcatgtgt atttccagtg ccaattgtag gggtgtgtgt    1644
gtgtgtgtgt gtgtgtgtgt atgactaaag agagaatgta gatattgtga agtacatatt    1704
aggaaaatat gggttgcatt tggtcaagat tttgaatgct tcctgacaat caactctaat    1764
agtgcttaaa aatcattgat tgtcagctac taatgatgtt ttcctataat ataataaata    1824
tttatgtaga tgtgcatttt tgtgaaatga aacatgtaa taaaagtat atgttaggat      1884 acaaat                                                               1890
```

<210> SEQ ID NO 25
<211> LENGTH: 281
<212> TYPE: PRT
<213> ORGANISM: Homo sapiens

<400> SEQUENCE: 25

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
        35                  40                  45

Pro Pro Pro Pro Pro Leu Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80
```

```
Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 26
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 26
ccatagctaa gggaaacacc                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
gccagcccca gcaaacggtt                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
tgcatggcag ctggtgagtc                                              20

<210> SEQ ID NO 29
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 29
ggaagaactg tgcctggagg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 30
tggcagcggt agtggaggca                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 31
gctgtgtgca tctggctggt                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 32
aatgggccac tttcctcagc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
gcaggttgtt gcaagattga                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 34
aagattgaac actgccccca                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 35
```
aatcccaaag tgcttctctt 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 36
ttctcggtgc ctgtaacaaa 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
gctacagaca ttttgaaccc 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
ccgtcatatt cctccatttg 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
ccctcttcac atggcagccc 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
ggtgtccttt tcaatctgcc 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
cagtccccct tgaggtagca 20

<210> SEQ ID NO 42
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 42
gtgaagatgc tgccagtggg                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
cccctacaat tggcactgga                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
tcttgaccaa atgcaaccca                                              20

<210> SEQ ID NO 45
<211> LENGTH: 8119
<212> TYPE: DNA
<213> ORGANISM: Homo sapiens
<220> FEATURE:
<221> NAME/KEY: CDS
<222> LOCATION: (64)..(7521)
<300> PUBLICATION INFORMATION:
<303> JOURNAL: FEBS Lett.
<304> VOLUME: 337
<305> ISSUE: 2
<306> PAGES: 200-206
<307> DATE: 1994-01-10
<308> DATABASE ACCESSION NUMBER: D21209/Genbank
<309> DATABASE ENTRY DATE: 1999-02-05

<400> SEQUENCE: 45
cgtccctgca gccctcgccc ggcgctccag tagcaggacc cggtctcggg accagccggt    60 aat atg cac gtg tca cta gct gag gcc ctg gag gtt cgg ggt gga cca   108
    Met His Val Ser Leu Ala Glu Ala Leu Glu Val Arg Gly Gly Pro
      1               5                  10                  15 ctt cag gag gaa gaa ata tgg gct gta tta aat caa agt gct gaa agt   156
Leu Gln Glu Glu Glu Ile Trp Ala Val Leu Asn Gln Ser Ala Glu Ser
                 20                  25                  30 ctc caa gaa tta ttc aga aaa gta agc cta gct gat cct gct gcc ctt   204
Leu Gln Glu Leu Phe Arg Lys Val Ser Leu Ala Asp Pro Ala Ala Leu
             35                  40                  45 ggc ttc atc att tct cca tgg tct ctg ctg ttg ctg cca tct ggt agt   252
Gly Phe Ile Ile Ser Pro Trp Ser Leu Leu Leu Leu Pro Ser Gly Ser
         50                  55                  60 gtg tca ttt aca gat gaa aat att tcc aat cag gat ctt cga gca ttc   300
Val Ser Phe Thr Asp Glu Asn Ile Ser Asn Gln Asp Leu Arg Ala Phe
     65                  70                  75 act gca cca gag gtt ctt caa aat cag tca cta act tct ctc tca gat   348
Thr Ala Pro Glu Val Leu Gln Asn Gln Ser Leu Thr Ser Leu Ser Asp
 80                  85                  90                  95 gtt gaa aag atc cac att tat tct ctt gga atg aca ctg tat tgg ggg   396
Val Glu Lys Ile His Ile Tyr Ser Leu Gly Met Thr Leu Tyr Trp Gly
                    100                 105                 110
```

| | | |
|---|---|---|
| gct gat tat gaa gtg cct cag agc caa cct att aag ctt gga gat cat<br>Ala Asp Tyr Glu Val Pro Gln Ser Gln Pro Ile Lys Leu Gly Asp His<br>115 120 125 | | 444 |
| ctc aac agc ata ctg ctt gga atg tgt gag gat gtt att tac gct cga<br>Leu Asn Ser Ile Leu Leu Gly Met Cys Glu Asp Val Ile Tyr Ala Arg<br>130 135 140 | | 492 |
| gtt tct gtt cgg act gtg ctg gat gct tgc agt gcc cac att agg aat<br>Val Ser Val Arg Thr Val Leu Asp Ala Cys Ser Ala His Ile Arg Asn<br>145 150 155 | | 540 |
| agc aat tgt gca ccc tca ttt tcc tac gtg aaa cac ttg gta aaa ctg<br>Ser Asn Cys Ala Pro Ser Phe Ser Tyr Val Lys His Leu Val Lys Leu<br>160 165 170 175 | | 588 |
| gtt ctg gga aat ctt tct ggg aca gat cag ctt tcc tgt aac agt gaa<br>Val Leu Gly Asn Leu Ser Gly Thr Asp Gln Leu Ser Cys Asn Ser Glu<br>180 185 190 | | 636 |
| caa aag cct gat cga agc cag gct att cga gat cga ttg cga gga aaa<br>Gln Lys Pro Asp Arg Ser Gln Ala Ile Arg Asp Arg Leu Arg Gly Lys<br>195 200 205 | | 684 |
| gga tta cca aca gga aga agc tct act tct gat gta cta gac ata caa<br>Gly Leu Pro Thr Gly Arg Ser Ser Thr Ser Asp Val Leu Asp Ile Gln<br>210 215 220 | | 732 |
| aag cct cca ctc tct cat cag acc ttt ctt aac aaa ggg ctt agt aaa<br>Lys Pro Pro Leu Ser His Gln Thr Phe Leu Asn Lys Gly Leu Ser Lys<br>225 230 235 | | 780 |
| tct atg gga ttt ctg tcc atc aaa gat aca caa gat gag aat tat ttc<br>Ser Met Gly Phe Leu Ser Ile Lys Asp Thr Gln Asp Glu Asn Tyr Phe<br>240 245 250 255 | | 828 |
| aag gac att tta tca gat aat tct gga cgt gaa gat tct gaa aat aca<br>Lys Asp Ile Leu Ser Asp Asn Ser Gly Arg Glu Asp Ser Glu Asn Thr<br>260 265 270 | | 876 |
| ttc tcc cct tac cag ttc aaa act agt ggc cca gaa aaa aaa ccc atc<br>Phe Ser Pro Tyr Gln Phe Lys Thr Ser Gly Pro Glu Lys Lys Pro Ile<br>275 280 285 | | 924 |
| cct ggc att gat gtg ctt tct aag aag aag atc tgg gct tca tcc atg<br>Pro Gly Ile Asp Val Leu Ser Lys Lys Lys Ile Trp Ala Ser Ser Met<br>290 295 300 | | 972 |
| gac ttg ctt tgt aca gct gac aga gac ttc tct tca gga gag act gcc<br>Asp Leu Leu Cys Thr Ala Asp Arg Asp Phe Ser Ser Gly Glu Thr Ala<br>305 310 315 | | 1020 |
| aca tat cgt cgt tgt cac cct gag gca gta aca gtg cgg act tca act<br>Thr Tyr Arg Arg Cys His Pro Glu Ala Val Thr Val Arg Thr Ser Thr<br>320 325 330 335 | | 1068 |
| act cct aga aaa aag gag gca aga tac tca gat gga agt ata gcc ttg<br>Thr Pro Arg Lys Lys Glu Ala Arg Tyr Ser Asp Gly Ser Ile Ala Leu<br>340 345 350 | | 1116 |
| gat atc ttt ggc cct cag aaa atg gat cca ata tat cac act cga gaa<br>Asp Ile Phe Gly Pro Gln Lys Met Asp Pro Ile Tyr His Thr Arg Glu<br>355 360 365 | | 1164 |
| ttg ccc acc tcc tca gca ata tca agt gct ttg gac cga atc cga gag<br>Leu Pro Thr Ser Ser Ala Ile Ser Ser Ala Leu Asp Arg Ile Arg Glu<br>370 375 380 | | 1212 |
| aga caa aag aaa ctt cag gtt ctg agg gaa gcc atg aat gta gaa gaa<br>Arg Gln Lys Lys Leu Gln Val Leu Arg Glu Ala Met Asn Val Glu Glu<br>385 390 395 | | 1260 |
| cca gtt cga aga tac aaa act tat cat ggt gat gtc ttt agt acc tcc<br>Pro Val Arg Arg Tyr Lys Thr Tyr His Gly Asp Val Phe Ser Thr Ser<br>400 405 410 415 | | 1308 |
| agt gaa agt cca tct att att tcc tct gaa tca gat ttc aga caa gtg<br>Ser Glu Ser Pro Ser Ile Ile Ser Ser Glu Ser Asp Phe Arg Gln Val | | 1356 |

-continued

|   |   |   |   |   |   |   |   |   |   |   |   |   |   |   |   |   |
|---|---|---|---|---|---|---|---|---|---|---|---|---|---|---|---|---|
|   |   |   | 420 |   |   |   |   | 425 |   |   |   |   | 430 |   |   |   |
| aga | aga | agt | gaa | gcc | tca | aag | agg | ttt | gaa | tcc | agc | agt | ggt | ctc | cca | 1404 |
| Arg | Arg | Ser | Glu | Ala | Ser | Lys | Arg | Phe | Glu | Ser | Ser | Ser | Gly | Leu | Pro |   |
|   |   |   | 435 |   |   |   |   | 440 |   |   |   |   | 445 |   |   |   |
| ggg | gta | gat | gaa | acc | tta | agt | caa | ggc | cag | tca | cag | aga | ccg | agc | aga | 1452 |
| Gly | Val | Asp | Glu | Thr | Leu | Ser | Gln | Gly | Gln | Ser | Gln | Arg | Pro | Ser | Arg |   |
|   |   |   | 450 |   |   |   |   | 455 |   |   |   |   | 460 |   |   |   |
| caa | tat | gaa | aca | ccc | ttt | gaa | ggc | aac | tta | att | aat | caa | gag | atc | atg | 1500 |
| Gln | Tyr | Glu | Thr | Pro | Phe | Glu | Gly | Asn | Leu | Ile | Asn | Gln | Glu | Ile | Met |   |
|   |   |   | 465 |   |   |   |   | 470 |   |   |   |   | 475 |   |   |   |
| cta | aaa | cgg | caa | gag | gaa | gaa | ctg | atg | cag | cta | caa | gcc | aaa | atg | gcc | 1548 |
| Leu | Lys | Arg | Gln | Glu | Glu | Glu | Leu | Met | Gln | Leu | Gln | Ala | Lys | Met | Ala |   |
| 480 |   |   |   |   | 485 |   |   |   |   | 490 |   |   |   |   | 495 |   |
| ctt | aga | cag | tct | cgg | ttg | agc | cta | tat | cca | gga | gac | aca | atc | aaa | gcg | 1596 |
| Leu | Arg | Gln | Ser | Arg | Leu | Ser | Leu | Tyr | Pro | Gly | Asp | Thr | Ile | Lys | Ala |   |
|   |   |   |   | 500 |   |   |   |   | 505 |   |   |   |   | 510 |   |   |
| tcc | atg | ctt | gac | atc | acc | agg | gat | ccg | tta | aga | gaa | att | gcc | cta | gaa | 1644 |
| Ser | Met | Leu | Asp | Ile | Thr | Arg | Asp | Pro | Leu | Arg | Glu | Ile | Ala | Leu | Glu |   |
|   |   |   |   | 515 |   |   |   |   | 520 |   |   |   |   | 525 |   |   |
| aca | gcc | atg | act | caa | aga | aaa | ctg | agg | aat | ttc | ttt | ggc | cct | gag | ttt | 1692 |
| Thr | Ala | Met | Thr | Gln | Arg | Lys | Leu | Arg | Asn | Phe | Phe | Gly | Pro | Glu | Phe |   |
|   |   |   | 530 |   |   |   |   | 535 |   |   |   |   | 540 |   |   |   |
| gtg | aaa | atg | aca | att | gaa | cca | ttt | ata | tct | ttg | gat | ttg | cca | cgg | tct | 1740 |
| Val | Lys | Met | Thr | Ile | Glu | Pro | Phe | Ile | Ser | Leu | Asp | Leu | Pro | Arg | Ser |   |
|   |   |   | 545 |   |   |   |   | 550 |   |   |   |   | 555 |   |   |   |
| att | ctt | act | aag | aaa | ggg | aag | aat | gag | gat | aac | cga | agg | aaa | gta | aac | 1788 |
| Ile | Leu | Thr | Lys | Lys | Gly | Lys | Asn | Glu | Asp | Asn | Arg | Arg | Lys | Val | Asn |   |
| 560 |   |   |   |   | 565 |   |   |   |   | 570 |   |   |   |   | 575 |   |
| ata | atg | ctt | ctg | aac | ggg | caa | aga | ctg | gaa | ctg | acc | tgt | gat | acc | aaa | 1836 |
| Ile | Met | Leu | Leu | Asn | Gly | Gln | Arg | Leu | Glu | Leu | Thr | Cys | Asp | Thr | Lys |   |
|   |   |   |   | 580 |   |   |   |   | 585 |   |   |   |   | 590 |   |   |
| act | ata | tgt | aaa | gat | gtg | ttt | gat | atg | gtt | gtg | gca | cat | att | ggc | tta | 1884 |
| Thr | Ile | Cys | Lys | Asp | Val | Phe | Asp | Met | Val | Val | Ala | His | Ile | Gly | Leu |   |
|   |   |   |   | 595 |   |   |   |   | 600 |   |   |   |   | 605 |   |   |
| gta | gag | cat | cat | ttg | ttt | gct | tta | gct | acc | ctc | aaa | gat | aat | gaa | tat | 1932 |
| Val | Glu | His | His | Leu | Phe | Ala | Leu | Ala | Thr | Leu | Lys | Asp | Asn | Glu | Tyr |   |
|   |   |   | 610 |   |   |   |   | 615 |   |   |   |   | 620 |   |   |   |
| ttc | ttt | gtt | gat | cct | gac | tta | aaa | tta | acc | aaa | gtg | gcc | cca | gag | gga | 1980 |
| Phe | Phe | Val | Asp | Pro | Asp | Leu | Lys | Leu | Thr | Lys | Val | Ala | Pro | Glu | Gly |   |
|   |   |   | 625 |   |   |   |   | 630 |   |   |   |   | 635 |   |   |   |
| tgg | aaa | gaa | gaa | cca | aag | aaa | aag | acc | aaa | gcc | act | gtt | aat | ttt | act | 2028 |
| Trp | Lys | Glu | Glu | Pro | Lys | Lys | Lys | Thr | Lys | Ala | Thr | Val | Asn | Phe | Thr |   |
| 640 |   |   |   |   | 645 |   |   |   |   | 650 |   |   |   |   | 655 |   |
| ttg | ttt | ttc | aga | att | aaa | ttt | ttt | atg | gat | gat | gtt | agt | cta | ata | caa | 2076 |
| Leu | Phe | Phe | Arg | Ile | Lys | Phe | Phe | Met | Asp | Asp | Val | Ser | Leu | Ile | Gln |   |
|   |   |   | 660 |   |   |   |   | 665 |   |   |   |   | 670 |   |   |   |
| cat | act | ctg | acg | tgt | cat | cag | tat | tac | ctt | cag | ctt | cga | aaa | gat | att | 2124 |
| His | Thr | Leu | Thr | Cys | His | Gln | Tyr | Tyr | Leu | Gln | Leu | Arg | Lys | Asp | Ile |   |
|   |   |   |   | 675 |   |   |   |   | 680 |   |   |   |   | 685 |   |   |
| ttg | gag | gaa | agg | atg | cac | tgt | gat | gat | gag | act | tcc | tta | ttg | ctg | gca | 2172 |
| Leu | Glu | Glu | Arg | Met | His | Cys | Asp | Asp | Glu | Thr | Ser | Leu | Leu | Leu | Ala |   |
|   |   |   | 690 |   |   |   |   | 695 |   |   |   |   | 700 |   |   |   |
| tcc | ttg | gct | ctc | cag | gct | gag | tat | gga | gat | tat | caa | cca | gag | gtt | cat | 2220 |
| Ser | Leu | Ala | Leu | Gln | Ala | Glu | Tyr | Gly | Asp | Tyr | Gln | Pro | Glu | Val | His |   |
|   |   |   | 705 |   |   |   |   | 710 |   |   |   |   | 715 |   |   |   |
| ggt | gtg | tct | tac | ttt | aga | atg | gag | cac | tat | ttg | ccc | gcc | aga | gtg | atg | 2268 |
| Gly | Val | Ser | Tyr | Phe | Arg | Met | Glu | His | Tyr | Leu | Pro | Ala | Arg | Val | Met |   |
| 720 |   |   |   |   | 725 |   |   |   |   | 730 |   |   |   |   | 735 |   |
| gag | aaa | ctt | gat | tta | tcc | tat | atc | aaa | gaa | gag | tta | ccc | aaa | ttg | cat | 2316 |

-continued

```
                    Glu Lys Leu Asp Leu Ser Tyr Ile Lys Glu Glu Leu Pro Lys Leu His
                                        740                 745                 750 aat acc tat gtg gga gct tct gaa aaa gag aca gag tta gaa ttt tta        2364
Asn Thr Tyr Val Gly Ala Ser Glu Lys Glu Thr Glu Leu Glu Phe Leu
            755                 760                 765 aag gtc tgc caa aga ctg aca gaa tat gga gtt cat ttt cac cga gtg        2412
Lys Val Cys Gln Arg Leu Thr Glu Tyr Gly Val His Phe His Arg Val
    770                 775                 780 cac cct gag aag aag tca caa aca gga ata ttg ctt gga gtc tgt tct        2460
His Pro Glu Lys Lys Ser Gln Thr Gly Ile Leu Leu Gly Val Cys Ser
785                 790                 795 aaa ggt gtc ctt gtg ttt gaa gtt cac aat gga gtg cgc aca ttg gtc        2508
Lys Gly Val Leu Val Phe Glu Val His Asn Gly Val Arg Thr Leu Val
800                 805                 810                 815 ctt cgc ttt cca tgg agg gaa acc aag aaa ata tct ttt tct aaa aag        2556
Leu Arg Phe Pro Trp Arg Glu Thr Lys Lys Ile Ser Phe Ser Lys Lys
                820                 825                 830 aaa atc aca ttg caa aat aca tca gat gga ata aaa cat ggc ttc cag        2604
Lys Ile Thr Leu Gln Asn Thr Ser Asp Gly Ile Lys His Gly Phe Gln
            835                 840                 845 aca gac aac agt aag ata tgc cag tac ctg ctg cac ctc tgc tct tac        2652
Thr Asp Asn Ser Lys Ile Cys Gln Tyr Leu Leu His Leu Cys Ser Tyr
        850                 855                 860 cag cat aag ttc cag cta cag atg aga gca aga cag agc aac caa gat        2700
Gln His Lys Phe Gln Leu Gln Met Arg Ala Arg Gln Ser Asn Gln Asp
865                 870                 875 gcc caa gat att gag aga gct tcg ttt agg agc ctg aat ctc caa gca        2748
Ala Gln Asp Ile Glu Arg Ala Ser Phe Arg Ser Leu Asn Leu Gln Ala
880                 885                 890                 895 gag tct gtt aga gga ttt aat atg gga cga gca atc agc act ggc agt        2796
Glu Ser Val Arg Gly Phe Asn Met Gly Arg Ala Ile Ser Thr Gly Ser
                900                 905                 910 ctg gcc agc agc acc ctc aac aaa ctt gct gtt cga cct tta tca gtt        2844
Leu Ala Ser Ser Thr Leu Asn Lys Leu Ala Val Arg Pro Leu Ser Val
            915                 920                 925 caa gct gag att ctg aag agg cta tcc tgc tca gag ctg tcg ctt tac        2892
Gln Ala Glu Ile Leu Lys Arg Leu Ser Cys Ser Glu Leu Ser Leu Tyr
        930                 935                 940 cag cca ttg caa aac agt tca aaa gag aag aat gac aaa gct tca tgg        2940
Gln Pro Leu Gln Asn Ser Ser Lys Glu Lys Asn Asp Lys Ala Ser Trp
945                 950                 955 gag gaa aag cct aga gag atg agt aaa tca tac cat gat ctc agt cag        2988
Glu Glu Lys Pro Arg Glu Met Ser Lys Ser Tyr His Asp Leu Ser Gln
960                 965                 970                 975 gcc tct ctc tat cca cat cgg aaa aat gtc att gtt aac atg gaa ccc        3036
Ala Ser Leu Tyr Pro His Arg Lys Asn Val Ile Val Asn Met Glu Pro
                980                 985                 990 cca cca caa acc gtt gca gag ttg gtg gga aaa cct tct cac cag atg        3084
Pro Pro Gln Thr Val Ala Glu Leu Val Gly Lys Pro Ser His Gln Met
            995                 1000                1005 tca aga tct gat gca gaa tct ttg gca gga gtg aca aaa ctt aat aat        3132
Ser Arg Ser Asp Ala Glu Ser Leu Ala Gly Val Thr Lys Leu Asn Asn
        1010                1015                1020 tca aag tct gtt gcg agt tta aat aga agt cct gaa agg agg aaa cat        3180
Ser Lys Ser Val Ala Ser Leu Asn Arg Ser Pro Glu Arg Arg Lys His
    1025                1030                1035 gaa tca gac tcc tca tcc att gaa gac cct ggg caa gca tat gtt cta        3228
Glu Ser Asp Ser Ser Ser Ile Glu Asp Pro Gly Gln Ala Tyr Val Leu
1040                1045                1050                1055
```

-continued

| | |
|---|---|
| gga atg act atg cat agt tct gga aac tct tca tcc caa gta ccc tta<br>Gly Met Thr Met His Ser Ser Gly Asn Ser Ser Ser Gln Val Pro Leu<br>            1060                        1065                  1070 | 3276 |
| aaa gaa aat gat gtg cta cac aaa aga tgg agc ata gta tct tca cca<br>Lys Glu Asn Asp Val Leu His Lys Arg Trp Ser Ile Val Ser Ser Pro<br>1075                     1080                     1085 | 3324 |
| gaa agg gag atc acc tta gtg aac ctg aaa aaa gat gca aag tat ggc<br>Glu Arg Glu Ile Thr Leu Val Asn Leu Lys Lys Asp Ala Lys Tyr Gly<br>            1090                        1095                  1100 | 3372 |
| ttg gga ttt caa att att ggt ggg gag aag atg gga aga ctg gac cta<br>Leu Gly Phe Gln Ile Ile Gly Gly Glu Lys Met Gly Arg Leu Asp Leu<br>    1105                     1110                     1115 | 3420 |
| ggc ata ttt atc agt tca gtt gcc cct gga gga cca gct gac ttg gat<br>Gly Ile Phe Ile Ser Ser Val Ala Pro Gly Gly Pro Ala Asp Leu Asp<br>1120                     1125                     1130                  1135 | 3468 |
| gga tgc ttg aag cca gga gac cgt ttg ata tct gta aat agt gtg agt<br>Gly Cys Leu Lys Pro Gly Asp Arg Leu Ile Ser Val Asn Ser Val Ser<br>            1140                        1145                  1150 | 3516 |
| ctg gag gga gtc agc cac cat gct gca att gaa att ttg caa aat gca<br>Leu Glu Gly Val Ser His His Ala Ala Ile Glu Ile Leu Gln Asn Ala<br>    1155                     1160                     1165 | 3564 |
| cct gaa gat gtg aca ctt gtt atc tct cag cca aaa gaa aag ata tcc<br>Pro Glu Asp Val Thr Leu Val Ile Ser Gln Pro Lys Glu Lys Ile Ser<br>1170                     1175                     1180 | 3612 |
| aaa gtg cct tct act cct gtg cat ctc acc aat gag atg aaa aac tac<br>Lys Val Pro Ser Thr Pro Val His Leu Thr Asn Glu Met Lys Asn Tyr<br>            1185                        1190                  1195 | 3660 |
| atg aag aaa tct tcc tac atg caa gac agt gct ata gat tct tct tcc<br>Met Lys Lys Ser Ser Tyr Met Gln Asp Ser Ala Ile Asp Ser Ser Ser<br>1200                     1205                     1210                  1215 | 3708 |
| aag gat cac cac tgg tca cgt ggt acc ctg agg cac atc tcg gag aac<br>Lys Asp His His Trp Ser Arg Gly Thr Leu Arg His Ile Ser Glu Asn<br>            1220                        1225                  1230 | 3756 |
| tcc ttt ggg cca tct ggg ggc ctg cgg gaa gga agc ctg agt tct caa<br>Ser Phe Gly Pro Ser Gly Gly Leu Arg Glu Gly Ser Leu Ser Ser Gln<br>    1235                     1240                     1245 | 3804 |
| gat tcc agg act gag agt gcc agc ttg tct caa agc cag gtc aat ggt<br>Asp Ser Arg Thr Glu Ser Ala Ser Leu Ser Gln Ser Gln Val Asn Gly<br>1250                     1255                     1260 | 3852 |
| ttc ttt gcc agc cat tta ggt gac caa acc tgg cag gaa tca cag cat<br>Phe Phe Ala Ser His Leu Gly Asp Gln Thr Trp Gln Glu Ser Gln His<br>            1265                        1270                  1275 | 3900 |
| ggc agc cct tcc cca tct gta ata tcc aaa gcc acc gag aaa gag act<br>Gly Ser Pro Ser Pro Ser Val Ile Ser Lys Ala Thr Glu Lys Glu Thr<br>1280                     1285                     1290                  1295 | 3948 |
| ttc act gat agt aac caa agc aaa act aaa aag cca ggc att tct gat<br>Phe Thr Asp Ser Asn Gln Ser Lys Thr Lys Lys Pro Gly Ile Ser Asp<br>            1300                        1305                  1310 | 3996 |
| gta act gat tac tca gac cgt gga gat tca gac atg gat gaa gcc act<br>Val Thr Asp Tyr Ser Asp Arg Gly Asp Ser Asp Met Asp Glu Ala Thr<br>    1315                     1320                     1325 | 4044 |
| tac tcc agc agt cag gat cat caa aca cca aaa cag gaa tct tcc tct<br>Tyr Ser Ser Ser Gln Asp His Gln Thr Pro Lys Gln Glu Ser Ser Ser<br>1330                     1335                     1340 | 4092 |
| tca gtg aat aca tcc aac aag atg aat ttt aaa act ttt tct tca tca<br>Ser Val Asn Thr Ser Asn Lys Met Asn Phe Lys Thr Phe Ser Ser Ser<br>            1345                        1350                  1355 | 4140 |
| cct cct aag cct gga gat atc ttt gag gtt gaa ctg gct aaa aat gat<br>Pro Pro Lys Pro Gly Asp Ile Phe Glu Val Glu Leu Ala Lys Asn Asp<br>1360                     1365                     1370                  1375 | 4188 |

```
aac agc ttg ggg ata agt gtc acg gga ggt gtg aat acg agt gtc aga    4236
Asn Ser Leu Gly Ile Ser Val Thr Gly Gly Val Asn Thr Ser Val Arg
            1380                1385                1390 cat ggt ggc att tat gtg aaa gct gtt att ccc cag gga gca gca gag    4284
His Gly Gly Ile Tyr Val Lys Ala Val Ile Pro Gln Gly Ala Ala Glu
            1395                1400                1405 tct gat ggt aga att cac aaa ggt gat cgc gtc cta gct gtc aat gga    4332
Ser Asp Gly Arg Ile His Lys Gly Asp Arg Val Leu Ala Val Asn Gly
            1410                1415                1420 gtt agt cta gaa gga gcc acc cat aag caa gct gtg gaa aca ctg aga    4380
Val Ser Leu Glu Gly Ala Thr His Lys Gln Ala Val Glu Thr Leu Arg
            1425                1430                1435 aat aca gga cag gtg gtt cat ctg tta tta gaa aag gga caa tct cca    4428
Asn Thr Gly Gln Val Val His Leu Leu Leu Glu Lys Gly Gln Ser Pro
1440                1445                1450                1455 aca tct aaa gaa cat gtc ccg gta acc cca cag tgt acc ctt tca gat    4476
Thr Ser Lys Glu His Val Pro Val Thr Pro Gln Cys Thr Leu Ser Asp
                1460                1465                1470 cag aat gcc caa ggt caa ggc cca gaa aaa gtg aag aaa aca act cag    4524
Gln Asn Ala Gln Gly Gln Gly Pro Glu Lys Val Lys Lys Thr Thr Gln
            1475                1480                1485 gtc aaa gac tac agc ttt gtc act gaa gaa aat aca ttt gag gta aaa    4572
Val Lys Asp Tyr Ser Phe Val Thr Glu Glu Asn Thr Phe Glu Val Lys
            1490                1495                1500 tta ttt aaa aat agc tca ggt cta gga ttc agt ttt tct cga gaa gat    4620
Leu Phe Lys Asn Ser Ser Gly Leu Gly Phe Ser Phe Ser Arg Glu Asp
    1505                1510                1515 aat ctt ata ccg gag caa att aat gcc agc ata gta agg gtt aaa aag    4668
Asn Leu Ile Pro Glu Gln Ile Asn Ala Ser Ile Val Arg Val Lys Lys
1520                1525                1530                1535 ctc ttt cct gga cag cca gca gca gaa agt gga aaa att gat gta gga    4716
Leu Phe Pro Gly Gln Pro Ala Ala Glu Ser Gly Lys Ile Asp Val Gly
            1540                1545                1550 gat gtt atc ttg aaa gtg aat gga gcc tct ttg aaa gga cta tct cag    4764
Asp Val Ile Leu Lys Val Asn Gly Ala Ser Leu Lys Gly Leu Ser Gln
            1555                1560                1565 cag gaa gtc ata tct gct ctc agg gga act gct cca gaa gta ttc ttg    4812
Gln Glu Val Ile Ser Ala Leu Arg Gly Thr Ala Pro Glu Val Phe Leu
            1570                1575                1580 ctt ctc tgc aga cct cca cct ggt gtg cta ccg gaa att gat act gcg    4860
Leu Leu Cys Arg Pro Pro Pro Gly Val Leu Pro Glu Ile Asp Thr Ala
            1585                1590                1595 ctt ttg acc cca ctt cag tct cca gca caa gta ctt cca aac agc agt    4908
Leu Leu Thr Pro Leu Gln Ser Pro Ala Gln Val Leu Pro Asn Ser Ser
1600                1605                1610                1615 aaa gac tct tct cag cca tca tgt gtg gag caa agc acc agc tca gat    4956
Lys Asp Ser Ser Gln Pro Ser Cys Val Glu Gln Ser Thr Ser Ser Asp
            1620                1625                1630 gaa aat gaa atg tca gac aaa agc aaa aaa cag tgc aag tcc cca tcc    5004
Glu Asn Glu Met Ser Asp Lys Ser Lys Lys Gln Cys Lys Ser Pro Ser
            1635                1640                1645 aga aga gac agt tac agt gac agc agt ggg agt gga gaa gat gac tta    5052
Arg Arg Asp Ser Tyr Ser Asp Ser Ser Gly Ser Gly Glu Asp Asp Leu
            1650                1655                1660 gtg aca gct cca gca aac ata tca aat tcg acc tgg agt tca gct ttg    5100
Val Thr Ala Pro Ala Asn Ile Ser Asn Ser Thr Trp Ser Ser Ala Leu
            1665                1670                1675 cat cag act cta agc aac atg gta tca cag gca cag agt cat cat gaa    5148
His Gln Thr Leu Ser Asn Met Val Ser Gln Ala Gln Ser His His Glu
```

```
                          -continued
1680            1685            1690            1695 gca ccc aag agt caa gaa gat acc att tgt acc atg ttt tac tat cct    5196
Ala Pro Lys Ser Gln Glu Asp Thr Ile Cys Thr Met Phe Tyr Tyr Pro
        1700            1705            1710 cag aaa att ccc aat aaa cca gag ttt gag gac agt aat cct tcc cct    5244
Gln Lys Ile Pro Asn Lys Pro Glu Phe Glu Asp Ser Asn Pro Ser Pro
    1715            1720            1725 cta cca ccg gat atg gct cct ggg cag agt tat caa ccc caa tca gaa    5292
Leu Pro Pro Asp Met Ala Pro Gly Gln Ser Tyr Gln Pro Gln Ser Glu
        1730            1735            1740 tct gct tcc tct agt tcg atg gat aag tat cat ata cat cac att tct    5340
Ser Ala Ser Ser Ser Ser Met Asp Lys Tyr His Ile His His Ile Ser
    1745            1750            1755 gaa cca act aga caa gaa aac tgg aca cct ttg aaa aat gac ttg gaa    5388
Glu Pro Thr Arg Gln Glu Asn Trp Thr Pro Leu Lys Asn Asp Leu Glu
1760            1765            1770            1775 aat cac ctt gaa gac ttt gaa ctg gaa gta gaa ctc ctc att acc cta    5436
Asn His Leu Glu Asp Phe Glu Leu Glu Val Glu Leu Leu Ile Thr Leu
            1780            1785            1790 att aaa tca gaa aaa gga agc ctg ggt ttt aca gta acc aaa ggc aat    5484
Ile Lys Ser Glu Lys Gly Ser Leu Gly Phe Thr Val Thr Lys Gly Asn
        1795            1800            1805 cag aga att ggt tgt tat gtt cat gat gtc ata cag gat cca gcc aaa    5532
Gln Arg Ile Gly Cys Tyr Val His Asp Val Ile Gln Asp Pro Ala Lys
    1810            1815            1820 agt gat gga agg cta aaa cct ggg gac cgg ctc ata aag gtt aat gat    5580
Ser Asp Gly Arg Leu Lys Pro Gly Asp Arg Leu Ile Lys Val Asn Asp
        1825            1830            1835 aca gat gtt act aat atg act cat aca gat gca gtt aat ctg ctc cgg    5628
Thr Asp Val Thr Asn Met Thr His Thr Asp Ala Val Asn Leu Leu Arg
1840            1845            1850            1855 gct gca tcc aaa aca gtc aga tta gtt att gga cga gtt cta gaa tta    5676
Ala Ala Ser Lys Thr Val Arg Leu Val Ile Gly Arg Val Leu Glu Leu
            1860            1865            1870 ccc aga ata cca atg ttg cct cat ttg cta ccg gac ata aca cta acg    5724
Pro Arg Ile Pro Met Leu Pro His Leu Leu Pro Asp Ile Thr Leu Thr
        1875            1880            1885 tgc aac aaa gag gag ttg ggt ttt tcc tta tgt gga ggt cat gac agc    5772
Cys Asn Lys Glu Glu Leu Gly Phe Ser Leu Cys Gly Gly His Asp Ser
    1890            1895            1900 ctt tat caa gtg gta tat att agt gat att aat cca agg tcc gtc gca    5820
Leu Tyr Gln Val Val Tyr Ile Ser Asp Ile Asn Pro Arg Ser Val Ala
1905            1910            1915 gcc att gag ggt aat ctc cag cta tta gat gtc atc cat tat gtg aac    5868
Ala Ile Glu Gly Asn Leu Gln Leu Leu Asp Val Ile His Tyr Val Asn
1920            1925            1930            1935 gga gtc agc aca caa gga atg acc ttg gag gaa gtt aac aga gca tta    5916
Gly Val Ser Thr Gln Gly Met Thr Leu Glu Glu Val Asn Arg Ala Leu
            1940            1945            1950 gac atg tca ctt cct tca ttg gta ttg aaa gca aca aga aat gat ctt    5964
Asp Met Ser Leu Pro Ser Leu Val Leu Lys Ala Thr Arg Asn Asp Leu
        1955            1960            1965 cca gtg gtc ccc agc tca aag agg tct gct gtt tca gct cca aag tca    6012
Pro Val Val Pro Ser Ser Lys Arg Ser Ala Val Ser Ala Pro Lys Ser
    1970            1975            1980 acc aaa ggc aat ggt tcc tac agt gtg ggg tct tgc agc cag cct gcc    6060
Thr Lys Gly Asn Gly Ser Tyr Ser Val Gly Ser Cys Ser Gln Pro Ala
1985            1990            1995 ctc act cct aat gat tca ttc tcc acg gtt gct ggg gaa gaa ata aat    6108
```

```
Leu Thr Pro Asn Asp Ser Phe Ser Thr Val Ala Gly Glu Glu Ile Asn
2000                 2005                2010                2015 gaa ata tcg tac ccc aaa gga aaa tgt tct act tat cag ata aag gga        6156
Glu Ile Ser Tyr Pro Lys Gly Lys Cys Ser Thr Tyr Gln Ile Lys Gly
            2020                2025                2030 tca cca aac ttg act ctg ccc aaa gaa tct tat ata caa gaa gat gac        6204
Ser Pro Asn Leu Thr Leu Pro Lys Glu Ser Tyr Ile Gln Glu Asp Asp
                2035                2040                2045 att tat gat gat tcc caa gaa gct gaa gtt atc cag tct ctg ctg gat        6252
Ile Tyr Asp Asp Ser Gln Glu Ala Glu Val Ile Gln Ser Leu Leu Asp
    2050                2055                2060 gtt gtg gat gag gaa gcc cag aat ctt tta aac gaa aat aat gca gca        6300
Val Val Asp Glu Glu Ala Gln Asn Leu Leu Asn Glu Asn Asn Ala Ala
2065                2070                2075 gga tac tcc tgt ggt cca ggt aca tta aag atg aat ggg aag tta tca        6348
Gly Tyr Ser Cys Gly Pro Gly Thr Leu Lys Met Asn Gly Lys Leu Ser
2080                2085                2090                2095 gaa gag aga aca gaa gat aca gac tgc gat ggt tca cct tta cct gag        6396
Glu Glu Arg Thr Glu Asp Thr Asp Cys Asp Gly Ser Pro Leu Pro Glu
                2100                2105                2110 tat ttt act gag gcc acc aaa atg aat ggc tgt gaa gaa tat tgt gaa        6444
Tyr Phe Thr Glu Ala Thr Lys Met Asn Gly Cys Glu Glu Tyr Cys Glu
            2115                2120                2125 gaa aaa gta aaa agt gaa agc tta att cag aag cca caa gaa aag aag        6492
Glu Lys Val Lys Ser Glu Ser Leu Ile Gln Lys Pro Gln Glu Lys Lys
        2130                2135                2140 act gat gat gat gaa ata aca tgg gga aat gat gag ttg cca ata gag        6540
Thr Asp Asp Asp Glu Ile Thr Trp Gly Asn Asp Glu Leu Pro Ile Glu
2145                2150                2155 aga aca aac cat gaa gat tct gat aaa gat cat tcc ttt ctg aca aac        6588
Arg Thr Asn His Glu Asp Ser Asp Lys Asp His Ser Phe Leu Thr Asn
2160                2165                2170                2175 gat gag ctc gct gta ctc cct gtc gtc aaa gtg ctt ccc tct ggt aaa        6636
Asp Glu Leu Ala Val Leu Pro Val Val Lys Val Leu Pro Ser Gly Lys
                2180                2185                2190 tac acg ggt gcc aac tta aaa tca gtc att cga gtc ctg cgg ggt ttg        6684
Tyr Thr Gly Ala Asn Leu Lys Ser Val Ile Arg Val Leu Arg Gly Leu
            2195                2200                2205 cta gat caa gga att cct tct aag gag ctg gag aat ctt caa gaa tta        6732
Leu Asp Gln Gly Ile Pro Ser Lys Glu Leu Glu Asn Leu Gln Glu Leu
        2210                2215                2220 aaa cct ttg gat cag tgt cta att ggg caa act aag gaa aac aga agg        6780
Lys Pro Leu Asp Gln Cys Leu Ile Gly Gln Thr Lys Glu Asn Arg Arg
2225                2230                2235 aag aac aga tat aaa aat ata ctt ccc tat gat gct aca aga gtg cct        6828
Lys Asn Arg Tyr Lys Asn Ile Leu Pro Tyr Asp Ala Thr Arg Val Pro
2240                2245                2250                2255 ctt gga gat gaa ggt ggc tat atc aat gcc agc ttc att aag ata cca        6876
Leu Gly Asp Glu Gly Gly Tyr Ile Asn Ala Ser Phe Ile Lys Ile Pro
                2260                2265                2270 gtt ggg aaa gaa gag ttc gtt tac att gcc tgc caa gga cca ctg cct        6924
Val Gly Lys Glu Glu Phe Val Tyr Ile Ala Cys Gln Gly Pro Leu Pro
            2275                2280                2285 aca act gtt gga gac ttc tgg cag atg att tgg gag caa aaa tcc aca        6972
Thr Thr Val Gly Asp Phe Trp Gln Met Ile Trp Glu Gln Lys Ser Thr
        2290                2295                2300 gtg ata gcc atg atg act caa gaa gta gaa gga gaa aaa atc aaa tgc        7020
Val Ile Ala Met Met Thr Gln Glu Val Glu Gly Glu Lys Ile Lys Cys
2305                2310                2315
```

```
cag cgc tat tgg ccc aac atc cta ggc aaa aca aca atg gtc agc aac    7068
Gln Arg Tyr Trp Pro Asn Ile Leu Gly Lys Thr Thr Met Val Ser Asn
        2320            2325                2330                2335 aga ctt cga ctg gct ctt gtg aga atg cag cag ctg aag ggc ttt gtg    7116
Arg Leu Arg Leu Ala Leu Val Arg Met Gln Gln Leu Lys Gly Phe Val
                2340                2345                2350 gtg agg gca atg acc ctt gaa gat att cag acc aga gag gtg cgc cat    7164
Val Arg Ala Met Thr Leu Glu Asp Ile Gln Thr Arg Glu Val Arg His
            2355                2360                2365 att tct cat ctg aat ttc act gcc tgg cca gac cat gat aca cct tct    7212
Ile Ser His Leu Asn Phe Thr Ala Trp Pro Asp His Asp Thr Pro Ser
        2370                2375                2380 caa cca gat gat ctg ctt act ttt atc tcc tac atg aga cac atc cac    7260
Gln Pro Asp Asp Leu Leu Thr Phe Ile Ser Tyr Met Arg His Ile His
    2385                2390                2395 aga tca ggc cca atc att acg cac tgc agt gct ggc att gga cgt tca    7308
Arg Ser Gly Pro Ile Ile Thr His Cys Ser Ala Gly Ile Gly Arg Ser
2400                2405                2410                2415 ggg acc ctg att tgc ata gat gtg gtt ctg gga tta atc agt cag gat    7356
Gly Thr Leu Ile Cys Ile Asp Val Val Leu Gly Leu Ile Ser Gln Asp
                2420                2425                2430 ctt gat ttt gac atc tct gat ttg gtg cgc tgc atg aga cta caa aga    7404
Leu Asp Phe Asp Ile Ser Asp Leu Val Arg Cys Met Arg Leu Gln Arg
            2435                2440                2445 cac gga atg gtt cag aca gag gat caa tat att ttc tgc tat caa gtc    7452
His Gly Met Val Gln Thr Glu Asp Gln Tyr Ile Phe Cys Tyr Gln Val
        2450                2455                2460 atc ctt tat gtc ctg aca cgt ctt caa gca gaa gaa gag caa aaa cag    7500
Ile Leu Tyr Val Leu Thr Arg Leu Gln Ala Glu Glu Glu Gln Lys Gln
    2465                2470                2475 cag cct cag ctt ctg aag tga catgaaaaga gcctctggat gcatttccat       7551
Gln Pro Gln Leu Leu Lys
2480            2485 ttctctcctt aacctccagc agactcctgc tctctatcca aaataaagat cacagagcag   7611
caagttcata caacatgcat gttctcctct atcttagagg ggtattcttc ttgaaaataa   7671
aaaatattga aatgctgtat ttttacagct actttaacct atgataatta tttacaaaat   7731
tttaacacta accaaacaat gcagatctta gggatgatta aaggcagcat tgatgatag    7791 cagacattgt tacaaggaca tggtgagtct attttttaatg caccaatctt gtttatagca   7851
aaaatgtttt ccaatatttt aataaagtag ttattttata ggggatactt gaaaccagta   7911
tttaagcttt aaatgacagt aatattggca tagaaaaaag tagcaaatgt ttactgtatc   7971
aatttctaat gtttactata tagaatttcc tgtaatatat ttatatactt tttcatgaaa   8031
atggagttat cagttatctg tttgttactg catcatctgt ttgtaatcat tatctcactt   8091
tgtaaataaa aacacacctt aaaacatg                                      8119
```

<210> SEQ ID NO 46
<211> LENGTH: 2485
<212> TYPE: PRT
<213> ORGANISM: Homo sapiens

<400> SEQUENCE: 46

```
Met His Val Ser Leu Ala Glu Ala Leu Glu Val Arg Gly Gly Pro Leu
 1               5                   10                  15

Gln Glu Glu Glu Ile Trp Ala Val Leu Asn Gln Ser Ala Glu Ser Leu
            20                  25                  30

Gln Glu Leu Phe Arg Lys Val Ser Leu Ala Asp Pro Ala Ala Leu Gly
```

-continued

```
                 35                  40                  45
Phe Ile Ile Ser Pro Trp Ser Leu Leu Leu Pro Ser Gly Ser Val
                50                  55                  60
Ser Phe Thr Asp Glu Asn Ile Ser Asn Gln Asp Leu Arg Ala Phe Thr
 65                  70                  75                  80
Ala Pro Glu Val Leu Gln Asn Gln Ser Leu Thr Ser Leu Ser Asp Val
                 85                  90                  95
Glu Lys Ile His Ile Tyr Ser Leu Gly Met Thr Leu Tyr Trp Gly Ala
                100                 105                 110
Asp Tyr Glu Val Pro Gln Ser Gln Pro Ile Lys Leu Gly Asp His Leu
                115                 120                 125
Asn Ser Ile Leu Leu Gly Met Cys Glu Asp Val Ile Tyr Ala Arg Val
130                 135                 140
Ser Val Arg Thr Val Leu Asp Ala Cys Ser Ala His Ile Arg Asn Ser
145                 150                 155                 160
Asn Cys Ala Pro Ser Phe Ser Tyr Val Lys His Leu Val Lys Leu Val
                165                 170                 175
Leu Gly Asn Leu Ser Gly Thr Asp Gln Leu Ser Cys Asn Ser Glu Gln
                180                 185                 190
Lys Pro Asp Arg Ser Gln Ala Ile Arg Asp Arg Leu Arg Gly Lys Gly
                195                 200                 205
Leu Pro Thr Gly Arg Ser Ser Thr Ser Asp Val Leu Asp Ile Gln Lys
                210                 215                 220
Pro Pro Leu Ser His Gln Thr Phe Leu Asn Lys Gly Leu Ser Lys Ser
225                 230                 235                 240
Met Gly Phe Leu Ser Ile Lys Asp Thr Gln Asp Glu Asn Tyr Phe Lys
                245                 250                 255
Asp Ile Leu Ser Asp Asn Ser Gly Arg Glu Asp Ser Glu Asn Thr Phe
                260                 265                 270
Ser Pro Tyr Gln Phe Lys Thr Ser Gly Pro Glu Lys Lys Pro Ile Pro
                275                 280                 285
Gly Ile Asp Val Leu Ser Lys Lys Lys Ile Trp Ala Ser Ser Met Asp
                290                 295                 300
Leu Leu Cys Thr Ala Asp Arg Asp Phe Ser Ser Gly Glu Thr Ala Thr
305                 310                 315                 320
Tyr Arg Arg Cys His Pro Glu Ala Val Thr Val Arg Thr Ser Thr Thr
                325                 330                 335
Pro Arg Lys Lys Glu Ala Arg Tyr Ser Asp Gly Ser Ile Ala Leu Asp
                340                 345                 350
Ile Phe Gly Pro Gln Lys Met Asp Pro Ile Tyr His Thr Arg Glu Leu
                355                 360                 365
Pro Thr Ser Ser Ala Ile Ser Ser Ala Leu Asp Arg Ile Arg Glu Arg
                370                 375                 380
Gln Lys Lys Leu Gln Val Leu Arg Glu Ala Met Asn Val Glu Glu Pro
385                 390                 395                 400
Val Arg Arg Tyr Lys Thr Tyr His Gly Asp Val Phe Ser Thr Ser Ser
                405                 410                 415
Glu Ser Pro Ser Ile Ile Ser Ser Glu Ser Asp Phe Arg Gln Val Arg
                420                 425                 430
Arg Ser Glu Ala Ser Lys Arg Phe Glu Ser Ser Gly Leu Pro Gly
                435                 440                 445
Val Asp Glu Thr Leu Ser Gln Gly Gln Ser Gln Arg Pro Ser Arg Gln
450                 455                 460
```

```
Tyr Glu Thr Pro Phe Glu Gly Asn Leu Ile Asn Gln Glu Ile Met Leu
465                 470                 475                 480

Lys Arg Gln Glu Glu Glu Leu Met Gln Leu Gln Ala Lys Met Ala Leu
            485                 490                 495

Arg Gln Ser Arg Leu Ser Leu Tyr Pro Gly Asp Thr Ile Lys Ala Ser
        500                 505                 510

Met Leu Asp Ile Thr Arg Asp Pro Leu Arg Glu Ile Ala Leu Glu Thr
            515                 520                 525

Ala Met Thr Gln Arg Lys Leu Arg Asn Phe Phe Gly Pro Glu Phe Val
        530                 535                 540

Lys Met Thr Ile Glu Pro Phe Ile Ser Leu Asp Leu Pro Arg Ser Ile
545                 550                 555                 560

Leu Thr Lys Lys Gly Lys Asn Glu Asp Asn Arg Arg Lys Val Asn Ile
            565                 570                 575

Met Leu Leu Asn Gly Gln Arg Leu Glu Leu Thr Cys Asp Thr Lys Thr
        580                 585                 590

Ile Cys Lys Asp Val Phe Asp Met Val Ala His Ile Gly Leu Val
    595                 600                 605

Glu His His Leu Phe Ala Leu Ala Thr Leu Lys Asp Asn Glu Tyr Phe
    610                 615                 620

Phe Val Asp Pro Asp Leu Lys Leu Thr Lys Val Ala Pro Glu Gly Trp
625                 630                 635                 640

Lys Glu Glu Pro Lys Lys Lys Thr Lys Ala Thr Val Asn Phe Thr Leu
            645                 650                 655

Phe Phe Arg Ile Lys Phe Phe Met Asp Asp Val Ser Leu Ile Gln His
        660                 665                 670

Thr Leu Thr Cys His Gln Tyr Tyr Leu Gln Leu Arg Lys Asp Ile Leu
        675                 680                 685

Glu Glu Arg Met His Cys Asp Asp Glu Thr Ser Leu Leu Leu Ala Ser
        690                 695                 700

Leu Ala Leu Gln Ala Glu Tyr Gly Asp Tyr Gln Pro Glu Val His Gly
705                 710                 715                 720

Val Ser Tyr Phe Arg Met Glu His Tyr Leu Pro Ala Arg Val Met Glu
            725                 730                 735

Lys Leu Asp Leu Ser Tyr Ile Lys Glu Glu Leu Pro Lys Leu His Asn
        740                 745                 750

Thr Tyr Val Gly Ala Ser Glu Lys Glu Thr Glu Leu Glu Phe Leu Lys
        755                 760                 765

Val Cys Gln Arg Leu Thr Glu Tyr Gly Val His Phe His Arg Val His
770                 775                 780

Pro Glu Lys Lys Ser Gln Thr Gly Ile Leu Leu Gly Val Cys Ser Lys
785                 790                 795                 800

Gly Val Leu Val Phe Glu Val His Asn Gly Val Arg Thr Leu Val Leu
            805                 810                 815

Arg Phe Pro Trp Arg Glu Thr Lys Lys Ile Ser Phe Ser Lys Lys Lys
        820                 825                 830

Ile Thr Leu Gln Asn Thr Ser Asp Gly Ile Lys His Gly Phe Gln Thr
        835                 840                 845

Asp Asn Ser Lys Ile Cys Gln Tyr Leu Leu His Leu Cys Ser Tyr Gln
850                 855                 860

His Lys Phe Gln Leu Gln Met Arg Ala Arg Gln Ser Asn Gln Asp Ala
865                 870                 875                 880
```

-continued

```
Gln Asp Ile Glu Arg Ala Ser Phe Arg Ser Leu Asn Leu Gln Ala Glu
            885                 890                 895

Ser Val Arg Gly Phe Asn Met Gly Arg Ala Ile Ser Thr Gly Ser Leu
        900                 905                 910

Ala Ser Ser Thr Leu Asn Lys Leu Ala Val Arg Pro Leu Ser Val Gln
    915                 920                 925

Ala Glu Ile Leu Lys Arg Leu Ser Cys Ser Glu Leu Ser Leu Tyr Gln
930                 935                 940

Pro Leu Gln Asn Ser Ser Lys Glu Lys Asn Asp Lys Ala Ser Trp Glu
945                 950                 955                 960

Glu Lys Pro Arg Glu Met Ser Lys Ser Tyr His Asp Leu Ser Gln Ala
            965                 970                 975

Ser Leu Tyr Pro His Arg Lys Asn Val Ile Val Asn Met Glu Pro Pro
        980                 985                 990

Pro Gln Thr Val Ala Glu Leu Val Gly Lys Pro Ser His Gln Met Ser
    995                 1000                1005

Arg Ser Asp Ala Glu Ser Leu Ala Gly Val Thr Lys Leu Asn Asn Ser
    1010                1015                1020

Lys Ser Val Ala Ser Leu Asn Arg Ser Pro Glu Arg Arg Lys His Glu
025                 1030                1035                1040

Ser Asp Ser Ser Ile Glu Asp Pro Gly Gln Ala Tyr Val Leu Gly
            1045                1050                1055

Met Thr Met His Ser Ser Gly Asn Ser Ser Gln Val Pro Leu Lys
        1060                1065                1070

Glu Asn Asp Val Leu His Lys Arg Trp Ser Ile Val Ser Ser Pro Glu
    1075                1080                1085

Arg Glu Ile Thr Leu Val Asn Leu Lys Lys Asp Ala Lys Tyr Gly Leu
    1090                1095                1100

Gly Phe Gln Ile Ile Gly Gly Glu Lys Met Gly Arg Leu Asp Leu Gly
105                 1110                1115                1120

Ile Phe Ile Ser Ser Val Ala Pro Gly Gly Pro Ala Asp Leu Asp Gly
        1125                1130                1135

Cys Leu Lys Pro Gly Asp Arg Leu Ile Ser Val Asn Ser Val Ser Leu
        1140                1145                1150

Glu Gly Val Ser His His Ala Ala Ile Glu Ile Leu Gln Asn Ala Pro
    1155                1160                1165

Glu Asp Val Thr Leu Val Ile Ser Gln Pro Lys Glu Lys Ile Ser Lys
    1170                1175                1180

Val Pro Ser Thr Pro Val His Leu Thr Asn Glu Met Lys Asn Tyr Met
185                 1190                1195                1200

Lys Lys Ser Ser Tyr Met Gln Asp Ser Ala Ile Asp Ser Ser Lys
            1205                1210                1215

Asp His His Trp Ser Arg Gly Thr Leu Arg His Ile Ser Glu Asn Ser
            1220                1225                1230

Phe Gly Pro Ser Gly Leu Arg Glu Gly Ser Leu Ser Ser Gln Asp
    1235                1240                1245

Ser Arg Thr Glu Ser Ala Ser Leu Ser Gln Ser Gln Val Asn Gly Phe
    1250                1255                1260

Phe Ala Ser His Leu Gly Asp Gln Thr Trp Gln Glu Ser Gln His Gly
265                 1270                1275                1280

Ser Pro Ser Pro Ser Val Ile Ser Lys Ala Thr Glu Lys Glu Thr Phe
            1285                1290                1295

Thr Asp Ser Asn Gln Ser Lys Thr Lys Lys Pro Gly Ile Ser Asp Val
```

```
                1300                1305                1310
Thr Asp Tyr Ser Asp Arg Gly Asp Ser Asp Met Asp Glu Ala Thr Tyr
        1315                1320                1325

Ser Ser Ser Gln Asp His Gln Thr Pro Lys Gln Glu Ser Ser Ser Ser
1330                1335                1340

Val Asn Thr Ser Asn Lys Met Asn Phe Lys Thr Phe Ser Ser Ser Pro
345                 1350                1355                1360

Pro Lys Pro Gly Asp Ile Phe Glu Val Glu Leu Ala Lys Asn Asp Asn
        1365                1370                1375

Ser Leu Gly Ile Ser Val Thr Gly Gly Val Asn Thr Ser Val Arg His
        1380                1385                1390

Gly Gly Ile Tyr Val Lys Ala Val Ile Pro Gln Gly Ala Ala Glu Ser
        1395                1400                1405

Asp Gly Arg Ile His Lys Gly Asp Arg Val Leu Ala Val Asn Gly Val
        1410                1415                1420

Ser Leu Glu Gly Ala Thr His Lys Gln Ala Val Glu Thr Leu Arg Asn
425                 1430                1435                1440

Thr Gly Gln Val Val His Leu Leu Leu Glu Lys Gly Gln Ser Pro Thr
        1445                1450                1455

Ser Lys Glu His Val Pro Val Thr Pro Gln Cys Thr Leu Ser Asp Gln
        1460                1465                1470

Asn Ala Gln Gly Gln Gly Pro Glu Lys Val Lys Lys Thr Thr Gln Val
        1475                1480                1485

Lys Asp Tyr Ser Phe Val Thr Glu Glu Asn Thr Phe Glu Val Lys Leu
        1490                1495                1500

Phe Lys Asn Ser Ser Gly Leu Gly Phe Ser Phe Ser Arg Glu Asp Asn
505                 1510                1515                1520

Leu Ile Pro Glu Gln Ile Asn Ala Ser Ile Val Arg Val Lys Lys Leu
        1525                1530                1535

Phe Pro Gly Gln Pro Ala Ala Glu Ser Gly Lys Ile Asp Val Gly Asp
        1540                1545                1550

Val Ile Leu Lys Val Asn Gly Ala Ser Leu Lys Gly Leu Ser Gln Gln
        1555                1560                1565

Glu Val Ile Ser Ala Leu Arg Gly Thr Ala Pro Glu Val Phe Leu Leu
        1570                1575                1580

Leu Cys Arg Pro Pro Gly Val Leu Pro Glu Ile Asp Thr Ala Leu
585                 1590                1595                1600

Leu Thr Pro Leu Gln Ser Pro Ala Gln Val Leu Pro Asn Ser Ser Lys
                1605                1610                1615

Asp Ser Ser Gln Pro Ser Cys Val Glu Gln Ser Thr Ser Ser Asp Glu
        1620                1625                1630

Asn Glu Met Ser Asp Lys Ser Lys Lys Gln Cys Lys Ser Pro Ser Arg
        1635                1640                1645

Arg Asp Ser Tyr Ser Asp Ser Ser Gly Ser Gly Glu Asp Asp Leu Val
        1650                1655                1660

Thr Ala Pro Ala Asn Ile Ser Asn Ser Thr Trp Ser Ser Ala Leu His
665                 1670                1675                1680

Gln Thr Leu Ser Asn Met Val Ser Gln Ala Gln Ser His His Glu Ala
        1685                1690                1695

Pro Lys Ser Gln Glu Asp Thr Ile Cys Thr Met Phe Tyr Tyr Pro Gln
            1700                1705                1710

Lys Ile Pro Asn Lys Pro Glu Phe Glu Asp Ser Asn Pro Ser Pro Leu
        1715                1720                1725
```

-continued

```
Pro Pro Asp Met Ala Pro Gly Gln Ser Tyr Gln Pro Gln Ser Glu Ser
        1730                1735                1740

Ala Ser Ser Ser Met Asp Lys Tyr His Ile His His Ile Ser Glu
745                 1750                1755                1760

Pro Thr Arg Gln Glu Asn Trp Thr Pro Leu Lys Asn Asp Leu Glu Asn
            1765                1770                1775

His Leu Glu Asp Phe Glu Leu Glu Val Glu Leu Leu Ile Thr Leu Ile
            1780                1785                1790

Lys Ser Glu Lys Gly Ser Leu Gly Phe Thr Val Thr Lys Gly Asn Gln
        1795                1800                1805

Arg Ile Gly Cys Tyr Val His Asp Val Ile Gln Asp Pro Ala Lys Ser
        1810                1815                1820

Asp Gly Arg Leu Lys Pro Gly Asp Arg Leu Ile Lys Val Asn Asp Thr
825                 1830                1835                1840

Asp Val Thr Asn Met Thr His Thr Asp Ala Val Asn Leu Leu Arg Ala
                1845                1850                1855

Ala Ser Lys Thr Val Arg Leu Val Ile Gly Arg Val Leu Glu Leu Pro
            1860                1865                1870

Arg Ile Pro Met Leu Pro His Leu Leu Pro Asp Ile Thr Leu Thr Cys
        1875                1880                1885

Asn Lys Glu Glu Leu Gly Phe Ser Leu Cys Gly Gly His Asp Ser Leu
    1890                1895                1900

Tyr Gln Val Val Tyr Ile Ser Asp Ile Asn Pro Arg Ser Val Ala Ala
905                 1910                1915                1920

Ile Glu Gly Asn Leu Gln Leu Leu Asp Val Ile His Tyr Val Asn Gly
            1925                1930                1935

Val Ser Thr Gln Gly Met Thr Leu Glu Glu Val Asn Arg Ala Leu Asp
        1940                1945                1950

Met Ser Leu Pro Ser Leu Val Leu Lys Ala Thr Arg Asn Asp Leu Pro
        1955                1960                1965

Val Val Pro Ser Ser Lys Arg Ser Ala Val Ser Ala Pro Lys Ser Thr
    1970                1975                1980

Lys Gly Asn Gly Ser Tyr Ser Val Gly Ser Cys Ser Gln Pro Ala Leu
985                 1990                1995                2000

Thr Pro Asn Asp Ser Phe Ser Thr Val Ala Gly Glu Glu Ile Asn Glu
            2005                2010                2015

Ile Ser Tyr Pro Lys Gly Lys Cys Ser Thr Tyr Gln Ile Lys Gly Ser
            2020                2025                2030

Pro Asn Leu Thr Leu Pro Lys Glu Ser Tyr Ile Gln Glu Asp Asp Ile
        2035                2040                2045

Tyr Asp Asp Ser Gln Glu Ala Glu Val Ile Gln Ser Leu Leu Asp Val
    2050                2055                2060

Val Asp Glu Glu Ala Gln Asn Leu Leu Asn Glu Asn Asn Ala Ala Gly
065                 2070                2075                2080

Tyr Ser Cys Gly Pro Gly Thr Leu Lys Met Asn Gly Lys Leu Ser Glu
            2085                2090                2095

Glu Arg Thr Glu Asp Thr Asp Cys Asp Gly Ser Pro Leu Pro Glu Tyr
        2100                2105                2110

Phe Thr Glu Ala Thr Lys Met Asn Gly Cys Glu Glu Tyr Cys Glu Glu
        2115                2120                2125

Lys Val Lys Ser Glu Ser Leu Ile Gln Lys Pro Gln Glu Lys Lys Thr
    2130                2135                2140
```

-continued

```
Asp Asp Asp Glu Ile Thr Trp Gly Asn Asp Glu Leu Pro Ile Glu Arg
145             2150                2155                2160

Thr Asn His Glu Asp Ser Asp Lys Asp His Ser Phe Leu Thr Asn Asp
            2165                2170                2175

Glu Leu Ala Val Leu Pro Val Lys Val Leu Pro Ser Gly Lys Tyr
        2180                2185                2190

Thr Gly Ala Asn Leu Lys Ser Val Ile Arg Val Leu Arg Gly Leu Leu
        2195                2200                2205

Asp Gln Gly Ile Pro Ser Lys Glu Leu Glu Asn Leu Gln Glu Leu Lys
    2210                2215                2220

Pro Leu Asp Gln Cys Leu Ile Gly Gln Thr Lys Glu Asn Arg Arg Lys
225             2230                2235                2240

Asn Arg Tyr Lys Asn Ile Leu Pro Tyr Asp Ala Thr Arg Val Pro Leu
            2245                2250                2255

Gly Asp Glu Gly Gly Tyr Ile Asn Ala Ser Phe Ile Lys Ile Pro Val
        2260                2265                2270

Gly Lys Glu Glu Phe Val Tyr Ile Ala Cys Gln Gly Pro Leu Pro Thr
        2275                2280                2285

Thr Val Gly Asp Phe Trp Gln Met Ile Trp Glu Gln Lys Ser Thr Val
    2290                2295                2300

Ile Ala Met Met Thr Gln Glu Val Glu Gly Glu Lys Ile Lys Cys Gln
305             2310                2315                2320

Arg Tyr Trp Pro Asn Ile Leu Gly Lys Thr Thr Met Val Ser Asn Arg
            2325                2330                2335

Leu Arg Leu Ala Leu Val Arg Met Gln Gln Leu Lys Gly Phe Val Val
        2340                2345                2350

Arg Ala Met Thr Leu Glu Asp Ile Gln Thr Arg Glu Val Arg His Ile
    2355                2360                2365

Ser His Leu Asn Phe Thr Ala Trp Pro Asp His Asp Thr Pro Ser Gln
    2370                2375                2380

Pro Asp Asp Leu Leu Thr Phe Ile Ser Tyr Met Arg His Ile His Arg
385             2390                2395                2400

Ser Gly Pro Ile Ile Thr His Cys Ser Ala Gly Ile Gly Arg Ser Gly
            2405                2410                2415

Thr Leu Ile Cys Ile Asp Val Val Leu Gly Leu Ile Ser Gln Asp Leu
        2420                2425                2430

Asp Phe Asp Ile Ser Asp Leu Val Arg Cys Met Arg Leu Gln Arg His
    2435                2440                2445

Gly Met Val Gln Thr Glu Asp Gln Tyr Ile Phe Cys Tyr Gln Val Ile
    2450                2455                2460

Leu Tyr Val Leu Thr Arg Leu Gln Ala Glu Glu Glu Gln Lys Gln Gln
465             2470                2475                2480

Pro Gln Leu Leu Lys
            2485

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
acgtgcatat taccggctgg                                            20
```

```
<210> SEQ ID NO 48
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 48
gagaaatgat gaagccaagg                                           20

<210> SEQ ID NO 49
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 49
gttggctctg aggcacttca                                           20

<210> SEQ ID NO 50
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 50
tttgtctctc tcggattcgg                                           20

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
gccaaagaaa ttcctcagtt                                           20

<210> SEQ ID NO 52
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 52
aaggatgcca gcaataagga                                           20

<210> SEQ ID NO 53
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 53
ggtcttcaat ggatgaggag                                           20

<210> SEQ ID NO 54
<211> LENGTH: 20
<212> TYPE: DNA
<213> ORGANISM: Artificial Sequence
<220> FEATURE:
<223> OTHER INFORMATION: Synthetic Sequence
```

-continued

```
<400> SEQUENCE: 54
gtggtgatcc ttggaagaag                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 55
tccactccca ctgctgtcac                                                    20

<210> SEQ ID NO 56
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 56
ttctctgatt gcctttggtt                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 57
gcaactcatc atttccccat                                                    20

<210> SEQ ID NO 58
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 58
ccagaggctc ttttcatgtc                                                    20

<210> SEQ ID NO 59
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 59
gcatccagag gctcttttca                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 60
gctggaggtt aaggagagaa                                                    20

<210> SEQ ID NO 61
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 61
tttggataga gagcaggagt                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 62
tttcaagaag aatacccta                                                20

<210> SEQ ID NO 63
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 63
gctgccttta atcatcccta                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 64
actggtttca agtatcccct                                               20

<210> SEQ ID NO 65
<211> LENGTH: 1480
<212> TYPE: DNA
<213> ORGANISM: Mus musculus
<220> FEATURE:
<221> NAME/KEY: CDS
<222> LOCATION: (50)..(1033)
<300> PUBLICATION INFORMATION:
<303> JOURNAL: J. Immunol.
<304> VOLUME: 148
<306> PAGES: 1274-1297
<307> DATE: 1992-02-15
<308> DATABASE ACCESSION NUMBER: M83649/Genbank
<309> DATABASE ENTRY DATE: 1994-04-18

<400> SEQUENCE: 65
gccgcaggct gcccacacag gccgcccgct gttttccctt gctgcagac atg ctg tgg   58
                                                     Met Leu Trp
                                                       1 atc tgg gct gtc ctg cct ctg gtg ctt gct ggc tca cag tta aga gtt   106
Ile Trp Ala Val Leu Pro Leu Val Leu Ala Gly Ser Gln Leu Arg Val
      5                  10                  15 cat act caa ggt act aat agc atc tcc gag agt tta aag ctg agg agg   154
His Thr Gln Gly Thr Asn Ser Ile Ser Glu Ser Leu Lys Leu Arg Arg
 20                  25                  30                  35 cgg gtt cat gaa act gat aaa aac tgc tca gaa gga tta tat caa gga   202
Arg Val His Glu Thr Asp Lys Asn Cys Ser Glu Gly Leu Tyr Gln Gly
                 40                  45                  50
```

```
ggc cca ttt tgc tgt caa cca tgc caa cct ggt aaa aaa aaa gtt gag      250
Gly Pro Phe Cys Cys Gln Pro Cys Gln Pro Gly Lys Lys Lys Val Glu
         55                  60                  65 gac tgc aaa atg aat ggg ggt aca cca acc tgt gcc cca tgc aca gaa      298
Asp Cys Lys Met Asn Gly Gly Thr Pro Thr Cys Ala Pro Cys Thr Glu
         70                  75                  80 ggg aag gag tac atg gac aag aac cat tat gct gat aaa tgc aga aga      346
Gly Lys Glu Tyr Met Asp Lys Asn His Tyr Ala Asp Lys Cys Arg Arg
         85                  90                  95 tgc aca ctc tgc gat gaa gag cat ggt tta gaa gtg gaa aca aac tgc      394
Cys Thr Leu Cys Asp Glu Glu His Gly Leu Glu Val Glu Thr Asn Cys
100                 105                 110                 115 acc ctg acc cag aat acc aag tgc aag tgc aaa cca gac ttc tac tgc      442
Thr Leu Thr Gln Asn Thr Lys Cys Lys Cys Lys Pro Asp Phe Tyr Cys
                120                 125                 130 gat tct cct ggc tgt gaa cac tgt gtt cgc tgc gcc tcg tgt gaa cat      490
Asp Ser Pro Gly Cys Glu His Cys Val Arg Cys Ala Ser Cys Glu His
                135                 140                 145 gga acc ctt gag cca tgc aca gca acc agc aat aca aac tgc agg aaa      538
Gly Thr Leu Glu Pro Cys Thr Ala Thr Ser Asn Thr Asn Cys Arg Lys
                150                 155                 160 caa agt ccc aga aat cgc cta tgg ttg ttg acc atc ctt gtt ttg tta      586
Gln Ser Pro Arg Asn Arg Leu Trp Leu Leu Thr Ile Leu Val Leu Leu
165                 170                 175 att cca ctt gta ttt ata tat cga aag tac cgg aaa aga aag tgc tgg      634
Ile Pro Leu Val Phe Ile Tyr Arg Lys Tyr Arg Lys Arg Lys Cys Trp
180                 185                 190                 195 aaa agg aga cag gat gac cct gaa tct aga acc tcc agt cgt gaa acc      682
Lys Arg Arg Gln Asp Asp Pro Glu Ser Arg Thr Ser Ser Arg Glu Thr
                200                 205                 210 ata cca atg aat gcc tca aat ctt agc ttg agt aaa tac atc ccg aga      730
Ile Pro Met Asn Ala Ser Asn Leu Ser Leu Ser Lys Tyr Ile Pro Arg
                215                 220                 225 att gct gaa gac atg aca atc cag gaa gct aaa aaa ttt gct cga gaa      778
Ile Ala Glu Asp Met Thr Ile Gln Glu Ala Lys Lys Phe Ala Arg Glu
                230                 235                 240 aat aac atc aag gag ggc aag ata gat gag atc atg cat gac agc atc      826
Asn Asn Ile Lys Glu Gly Lys Ile Asp Glu Ile Met His Asp Ser Ile
                245                 250                 255 caa gac aca gct gag cag aaa gtc cag ctg ctc ctg tgc tgg tac caa      874
Gln Asp Thr Ala Glu Gln Lys Val Gln Leu Leu Leu Cys Trp Tyr Gln
260                 265                 270                 275 tct cat ggg aag agt gat gca tat caa gat tta atc aag ggt ctc aaa      922
Ser His Gly Lys Ser Asp Ala Tyr Gln Asp Leu Ile Lys Gly Leu Lys
                280                 285                 290 aaa gcc gaa tgt cgc aga acc tta gat aaa ttt cag gac atg gtc cag      970
Lys Ala Glu Cys Arg Arg Thr Leu Asp Lys Phe Gln Asp Met Val Gln
                295                 300                 305 aag gac ctt gga aaa tca acc cca gac act gga aat gaa aat gaa gga     1018
Lys Asp Leu Gly Lys Ser Thr Pro Asp Thr Gly Asn Glu Asn Glu Gly
                310                 315                 320 caa tgt ctg gag tga aaactacctc agttccagcc atgaagagag gagagagcct     1073
Gln Cys Leu Glu
325 gccacccatg atggaaacaa aatgaatgcc aactgtattg acattggcaa ctcctggtgt   1133 gttctctttg ccagcaaatg gtagttgata ctcagtgagg gtcaaatgac tagcaggttc   1193 cagggactgc ttctgttatt ctctgcagtt gctgagatga accattttct ctgtctactg   1253 caatttttac attcaaatgt ccatgaaatt tgtattaaat gtgaagtgga atctgcagtg   1313
```

```
tttgtgttta tattcatata ctatgaactg aggagaatta taaactgaaa caaatactcg      1373
cagttaattg aagaccttcc attgatggac agttctttc ctctctatat ggaaatgtat       1433
aatagaagaa ataattttta aattaaagta tctcttttg catttca                     1480
```

<210> SEQ ID NO 66
<211> LENGTH: 327
<212> TYPE: PRT
<213> ORGANISM: Mus musculus

<400> SEQUENCE: 66

```
Met Leu Trp Ile Trp Ala Val Leu Pro Leu Val Leu Ala Gly Ser Gln
 1               5                  10                  15

Leu Arg Val His Thr Gln Gly Thr Asn Ser Ile Ser Glu Ser Leu Lys
            20                  25                  30

Leu Arg Arg Arg Val His Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Arg Lys Tyr Arg Lys Arg
            180                 185                 190

Lys Cys Trp Lys Arg Arg Gln Asp Asp Pro Glu Ser Arg Thr Ser Ser
        195                 200                 205

Arg Glu Thr Ile Pro Met Asn Ala Ser Asn Leu Ser Leu Ser Lys Tyr
    210                 215                 220

Ile Pro Arg Ile Ala Glu Asp Met Thr Ile Gln Glu Ala Lys Lys Phe
225                 230                 235                 240

Ala Arg Glu Asn Asn Ile Lys Glu Gly Lys Ile Asp Glu Ile Met His
                245                 250                 255

Asp Ser Ile Gln Asp Thr Ala Glu Gln Lys Val Gln Leu Leu Leu Cys
            260                 265                 270

Trp Tyr Gln Ser His Gly Lys Ser Asp Ala Tyr Gln Asp Leu Ile Lys
        275                 280                 285

Gly Leu Lys Lys Ala Glu Cys Arg Arg Thr Leu Asp Lys Phe Gln Asp
    290                 295                 300

Met Val Gln Lys Asp Leu Gly Lys Ser Thr Pro Asp Thr Gly Asn Glu
305                 310                 315                 320

Asn Glu Gly Gln Cys Leu Glu
                325
```

```
<210> SEQ ID NO 67
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 67
gcagcaaggg aaaacagcgg                                               20

<210> SEQ ID NO 68
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 68
ccacagcatg tctgcagcaa                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 69
tttcatgaac ccgcctcctc                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 70
gggtcagggt gcagtttgtt                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 71
gaggcgcagc gaacacagtg                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 72
cataggcgat ttctgggact                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic Sequence
```

-continued

<400> SEQUENCE: 73
tccagcactt tcttttccgg                                            20

<210> SEQ ID NO 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
ggtttcacga ctggaggttc                                            20

<210> SEQ ID NO 75
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 75
cttcagcaat tctcgggatg                                            20

<210> SEQ ID NO 76
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 76
gccctccttg atgttatttt                                            20

<210> SEQ ID NO 77
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 77
ggtaccagca caggagcagc                                            20

<210> SEQ ID NO 78
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 78
cggctttttt gagacccttg                                            20

<210> SEQ ID NO 79
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 79
gtgtctgggg ttgattttcc                                            20

<210> SEQ ID NO 80
<211> LENGTH: 20

```
<212> TYPE: DNA
<213> ORGANISM: Artificial Sequence
<220> FEATURE:
<223> OTHER INFORMATION: Synthetic Sequence

<400> SEQUENCE: 80
tctcctctct tcatggctgg                                                 20

<210> SEQ ID NO 81
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 81
ggcattcatt ttgtttccat                                                 20

<210> SEQ ID NO 82
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 82
tccctggaac ctgctagtca                                                 20

<210> SEQ ID NO 83
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 83
tcagcaactg cagagaataa                                                 20

<210> SEQ ID NO 84
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 84
gcagattcca cttcacattt                                                 20

<210> SEQ ID NO 85
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 85
aaggtcttca attaactgcg                                                 20
```

ANTISENSE INHIBITION OF FAS MEDIATED SIGNALING

FIELD OF THE INVENTION

This invention relates to compositions and methods for modulating expression of the human Fas, FasL and Fap-1 genes, which encode proteins involved in Fas mediated signal transduction and are implicated in disease. This invention is also directed to methods for inhibiting Fas, FasL or Fap-1-mediated signal transduction; these methods can be used diagnostically or therapeutically. Furthermore, this invention is directed to treatment of conditions associated with expression of the human Fas, FasL or Fap-1 genes.

BACKGROUND OF THE INVENTION

The Fas ligand (FasL, also CD95L or Apo-1L) belongs to the tumor necrosis factor (TNF) family. It associates with the Fas receptor (Fas, also CD95 or Apo-1). Both function primarily as membrane-bound cell-surface proteins. The interaction between Fas and FasL is a key regulator of apoptosis within the immune system. Binding of FasL by Fas triggers apoptosis. Since both Fas and FasL are typically membrane-bound, cells expressing either Fas or FasL generally must come into contact with cells expressing the other in order to induce cell death (Rowe, P. M., *Lancet*, 1996, 347, 1398). Under normal conditions, expression of the FasL is generally limited to activated T cells and macrophages. Fas is expressed in a variety of lymphoid and non-lymphoid cells including thymus, liver, heart and kidney (Watanabe-Fukunaga, R., et al., *J. Immunol.*, 1992, 148, 1274–1279).

Expression of FasL is involved in a number of cancers, including lymphomas, melanoma (Hahne, M., et al., *Science*, 1996, 274, 1363–1366), colon, hepatic and lung carcinomas and astrocytomas (Saas, P., et al., *J. Clin. Invest.*, 1997, 99, 1173–1178). It is thought that FasL expression by tumor cells is a mechanism by which they escape killing by the immune system and instead enables them to kill immune cells possessing Fas receptor on their surfaces (Walker, P. R., et al., *J. Immunol.*, 1997, 158, 4521–4524).

Fas and FasL are also involved in other diseases, including autoimmune and inflammatory diseases. These include Hashimoto's thyroiditis (Giordano, C., et al., *Science*, 1997, 275, 1189–1192), hepatitis (Kondo, T., et al., *Nat. Med.*, 1997, 3, 409–413), diabetes (Chervonsky, A. V., et al., *Cell*, 1997, 89, 17–24), myasthenia gravis (Moulian, N., et al., *Blood*, 1997, 89, 3287–3295), ulcerative colitis (Strater, J., et al., *Gastroenterology*, 1997, 113, 160–167), autoimmune gastritis (Nishio, A., et al., *Gastroenterology* 1996, 111, 959–967), Sjogren's syndrome (Kong, L., et al., *Arthritis Rheum.*, 1997, 40, 87–97) and HIV infection (Sieg, S., et al., *Proc. Natl. Acad. Sci (USA)*, 1997, 94, 5860–5865).

Fap-1 (Fas associated protein 1 or protein tyrosine phosphatase (PTP-BAS, type 1)) is a tyrosine phosphatase that binds with a negative regulatory element of Fas (Sato, T., et al., *Science*, 1995, 268, 411–415). It also is an inhibitor of Fas-mediated apoptosis and an important component of Fas mediated signaling. The presence of Fap-1 in tumor cell lines also correlated with resistance to Fas antibody. Takahashi, M. et al. (*Gan To Kagaku Ryoho*, 1997, 24, 222–228) found that Fap-1 was expressed in many colon cancer cell lines, but not in normal colon cells.

Several approaches have been used to study the interaction between Fas and FasL and could potentially be used for therapeutic purposes. One way to disrupt the balance (altered or normal) between Fas and FasL is to provide additional amounts of one of them. This approach has been used with soluble Fas by Kondo, T., et al. (*Nature Med.*, 1997, 3, 409–413) to prevent hepatitis in a transgenic mouse model and Cheng, J., et al. (*Science*, 1994, 263, 1759–1762) to inhibit Fas-mediated apoptosis in systemic lupus erythematosus. Arai, H., et al. (*Proc. Natl. Acad. Sci. USA*, 1997, 94, 13862–13867) used a somewhat different approach to increase FasL. An adenoviral expression vector containing FasL was used to infect tumor cells. The increased levels of FasL induced apoptosis and caused tumor regression.

Portions of these proteins could also be used. It was found that the three C-terminal amino acids of Fas were necessary and sufficient for binding to Fap-1 (Yanagisawa, J., et al., *J. Biol. Chem.*, 1997, 272, 8539–8545). Introduction of this peptide into a colon cancer cell line induced Fas-mediated apoptosis.

Monoclonal antibodies to Fas have been used extensively to induce apoptosis. Anti-Fas antibodies resulted in tumor regression in B cell tumors (Trauth B. C., et al., *Science*, 1989, 245, 301–305), adult T-cell leukemia (Debatin, K. M., et al., *Lancet*, 1990, 335, 497–500), gliomas (Weller, M., et al., *J. Clin. Invest.*, 1994, 94, 954–964), and colorectal cancer (Meterissian, S. H., *Ann. Surg. Oncol.*, 1997, 4, 169–175). Antibodies to Fas also killed HIV infected cells (Kobayashi, N., et al., *Proc. Natl. Acad. Sci USA*, 1990, 87, 9620–9624). Monoclonal antibodies have been used in combination with chemotherapeutic drugs to overcome drug resistance (Morimoto, H., et al., *Cancer Res.*, 1993, 53, 2591–2596), Nakamura, S., et al., *Anticancer Res.*, 1997, 17, 173–179) and Wakahara, Y., et al., *Oncology*, 1997, 54, 48–54).

Chemical agents have been used to inhibit FasL expression (Yang, Y., et al., *J. Exp. Med.*, 1995, 181, 1673–1682). Retinoic acid and corticosteroids inhibit the up-regulation of FasL.

An antisense RNA approach, involving the antisense expression of a significant portion of a gene, has been used to modulate expression of Fas and Fap-1. Herr, I. et al. (*EMBO J.*, 1997, 16, 6200–6208) expressed a 360 bp fragment of Fas in the antisense orientation to inhibit apoptosis. Freiss, G. et al. (*Mol. Endocrinol.*, 1998, 12, 568–579) expressed a greater than 600 bp fragment of Fap-1 to inhibit Fap-1 expression.

Oligonucleotides have also been used to modulate expression of FasL. A bifunctional ribozyme targeted to both perforin and FasL was designed to treat graft-versus-host disease (Du, Z., et al., *Biochem. Biophys. Res. Commun.*, 1996 226, 595–600). Antisense oligonucleotides have been used against both Fas and FasL. Yu, W. et al. (Cancer Res., 1999, 59, 953–961) used an oligonucleotide targeted to the translation initiation site of human Fas to reduce Fas mediated signaling in breast cancer cells. Lee, J., et al. (*Endocrinology*, 1997, 138, 2081–2088) used an oligonucleotide targeted to the translation initiation region of rat FasL to show that Fas system regulates spermatogenesis. Turley, J. M., et al. (*Cancer Res.*, 1997, 57, 881–890) used an oligonucleotide targeted to the translation initiation region of human FasL to show that the Fas system was involved in Vitamin E succinate mediated apoptosis of human breast cancer cells. O'Connell, J., et al. (*J. Exp. Med.*, 1996, 184, 1075–1082) used a model involving Jurkat T cells and SW620, a colon cancer cell line. The presence of FasL on SW620 causes apoptosis of Jurkat cells which possess the Fas receptor. Antisense oligonucleotides to either the FasL on SW620 or Fas on Jurkat cells could prevent apoptosis of the Jurkat cells. Oligonucleotides were designed to target sequences toward the 3' end of the coding region.

There remains a long-felt need for improved compositions and methods for inhibiting Fas, FasL and Fap-1 gene expression.

SUMMARY OF THE INVENTION

The present invention provides antisense compounds, including antisense oligonucleotides, which are targeted to nucleic acids encoding Fas, FasL and Fap-1 and are capable of modulating Fas mediated signaling. The present invention also provides chimeric oligonucleotides targeted to nucleic acids encoding human Fas, FasL and Fap-1 The compounds and compositions of the invention are believed to be useful both diagnostically and therapeutically, and are believed to be particularly useful in the methods of the present invention.

The present invention also comprises methods of modulating the Fas mediated signaling, in cells and tissues, using the antisense compounds of the invention. Methods of inhibiting Fas, FasL and Fap-1 expression are provided; these methods are believed to be useful both therapeutically and diagnostically. These methods are also useful as tools, for example, for detecting and determining the role of Fas, FasL and Fap-1 in various cell functions and physiological processes and conditions and for diagnosing conditions associated with expression of Fas, FasL or Fap-1.

The present invention also comprises methods for diagnosing and treating autoimmune and inflammatory diseases, particularly hepatitis, and cancers, including those of the colon, liver and lung, and lymphomas. These methods are believed to be useful, for example, in diagnosing Fas, FasL and Fap-1-associated disease progression. These methods employ the antisense compounds of the invention. These methods are believed to be useful both therapeutically, including prophylactically, and as clinical research and diagnostic tools.

DETAILED DESCRIPTION OF THE INVENTION

Fas, FasL and Fap-1 play important roles in signal transduction. Overexpression and/or constitutive activation of Fas, FasL or Fap-1 is associated with a number of autoimmune and inflammatory diseases, and cancers. As such, these proteins involved in signal transduction represent attractive targets for treatment of such diseases. In particular, modulation of the expression of Fas, FasL or Fap-1 may be useful for the treatment of diseases such as hepatitis, colon cancer, liver cancer, lung cancer and lymphomas.

The present invention employs antisense compounds, particularly oligonucleotides, for use in modulating the function of nucleic acid molecules encoding Fas, FasL and Fap-1, ultimately modulating the amount of Fas, FasL or Fap-1 produced. This is accomplished by providing oligonucleotides which specifically hybridize with nucleic acids, preferably mRNA, encoding Fas, FasL or Fap-1.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the targets are nucleic acids encoding Fas, FasL or Fap-1; in other words, a gene encoding Fas, FasL or Fap-1, or mRNA expressed from the Fas, FasL or Fap-1 gene. mRNA which encodes Fas, FasL or Fap-1 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'- UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Fas, FasL or Fap-1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5'or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon—exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of Fas, FasL or Fap-1. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The oligonucleotides of this invention can be used in diagnostics, therapeutics, prophylaxis, and as research reagents and in kits. Since the oligonucleotides of this invention hybridize to nucleic acids encoding Fas, FasL or Fap-1, sandwich, calorimetric and other assays can easily be constructed to exploit this fact. Provision of means for detecting hybridization of oligonucleotide with the Fas, FasL or Fap-1 genes or mRNA can routinely be accomplished. Such provision may include enzyme conjugation, radiolabelling or any other suitable detection systems. Kits for detecting the presence or absence of Fas, FasL or Fap-1 may also be prepared.

The present invention is also suitable for diagnosing abnormal inflammatory states or certain cancers in tissue or other samples from patients suspected of having an autoimmune or inflammatory disease such as hepatitis or cancers such as those of the colon, liver or lung, and lymphomas. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,306; 5,550,111; 5,563,253; 5,571, 799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. No. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—,—$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_2$ON($CH_3$)$_2$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, and 2'-dimethylaminoethoxyethoxy (2'-DMAEOE), i.e., 2'-O—CH$_2$—O—CH$_2$—N(CH$_3$)$_2$.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative U.S. patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, International Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat, Nos. 4,845,205; 5,130,302; 5,134,066; 5,175,273; 5,367, 066; 5,432,272; 5,457,187; 5,459,255; 5,484,908; 5,502, 177; 5,525,711; 5,552,540; 5,587,469; 5,594,121, 5,596, 091; 5,614,617; and 5,681,941. Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glycol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative U.S. patents that teach the preparation of such oligonucleotide conjugates include, but are not limited to, U.S. Pat. Nos. 4,828,979; 4,948,882; 5,218,105; 5,525, 465; 5,541,313; 5,545,730; 5,552,538; 5,578,717, 5,580, 731; 5,580,731; 5,591,584; 5,109,124; 5,118,802; 5,138, 045; 5,414,077; 5,486,603; 5,512,439; 5,578,718; 5,608, 046; 4,587,044; 4,605,735; 4,667,025; 4,762,779; 4,789, 737; 4,824,941; 4,835,263; 4,876,335; 4,904,582; 4,958, 013; 5,082,830; 5,112,963; 5,214,136; 5,082,830; 5,112, 963; 5,214,136; 5,245,022; 5,254,469; 5,258,506; 5,262, 536; 5,272,250; 5,292,873; 5,317,098; 5,371,241, 5,391, 723; 5,416,203, 5,451,463; 5,510,475; 5,512,667; 5,514, 785; 5,565,552; 5,567,810; 5,574,142; 5,585,481; 5,587, 371; 5,595,726; 5,597,696; 5,599,923; 5,599,928 and 5,688, 941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2-O-methoxyethyl-substituted), or vice-versa. In one embodiment, the oligonucleotides of the present invention contain a 2'-O-methoxyethyl (2O—CH$_2$CH$_2$OCH$_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH$_2$CH$_2$OCH$_3$) modification. Oligonucleotides comprising a plurality of nucleotide subunits having a 2'O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. "Pharmaceutically acceptable salts" are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The following examples illustrate the present invention and are not intended to limit the same.

EXAMPLES

Example 1
Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl- (DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (*Helv. Chim. Acta* 1995, 78, 486–506). For ease of synthesis, the last nucleotide may be a deoxynucleotide. 2'-O—$CH_2CH_2OCH_3$-cytosines may be 5-methyl cytosines.
Synthesis of 5-Methyl cytosine Monomers
2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

2'-O-(dimethylaminooxyethyl)nucleoside amidites

2'-(Dimethylaminooxyethoxy)nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy) ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 hr the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl)thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 hr, the reaction monitored by TLC (5% MeOH in $CH_2C_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (Acc. Chem. Res. 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al. (Science 1991, 254, 1497–1500).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al. (J. Biol. Chem. 1991, 266, 18162). Results obtained with HPLC-purified material were similar to those obtained with non-HPLC purified material.

Alternatively, oligonucleotides are synthesized in 96 well plate format via solid phase P(III) phosphoramidite chemistry on an automated synthesizer capable of assembling 96 sequences simultaneously in a standard 96 well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites are purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 2
Human Fas Oligonucleotide Sequences

Antisense oligonucleotides were designed to target human Fas. Target sequence data are from the APO-1 cDNA sequence published by Oehm, A., et al. (J. Biol. Chem., 1992, 267, 10709–10715); Genbank accession number X63717, provided herein as SEQ ID NO: 1. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 1.

The C8161 melanoma cell line was obtained from Welch D. R., et al. (Int. J. Cancer, 1991, 47, 227–237). C8161 cells were cultured in RPMI 1640 medium plus 10% fetal bovine serum (Hyclone, Logan, Utah).

C8161 cells ($5.5 \times 10^5$ cells) were plated onto 100 cm plates. Two days later, the cells were washed once with OPTIMEM™ (Life Technologies, Rockville, Md.), then transfected with 300 nM oligonucleotide and 15 μg/ml LIPOFECTIN® (Life Technologies, Rockville, Md.), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. The cells were incubated with oligonucleotide for four hours, after which the media was replaced with fresh media and the cells incubated for another 20 hours.

Total cellular RNA was isolated using the RNEASY® kit (Qiagen, Santa Clarita, Calif.). RNA was then separated on a 1% agarose gel, transferred to Hybond-N+ membrane (Amersham, Arlington Heights, Ill.), a positively charged nylon membrane, and probed. A Fas probe was generated by random primer labeling of a RT-PCR amplified fragment of Fas mRNA. A glyceraldehyde 3-phosphate dehydrogenase (G3PDH) probe was purchased from Clontech (Palo Alto, Calif.), Catalog Number 9805-1. The probes were labeled by random primer using the Large Fragment of DNA polymerase (Klenow fragment) (GIBCO BRL) as described in Maniatis, T., et al., Molecular Cloning: A Laboratory Manual, 1989. mRNA was quantitated by a PhosphoImager (Molecular Dynamics, Sunnyvale, Calif.).

Results of an initial screen of Fas antisense oligonucleotides is shown in Table 2. Oligonucleotides 17014 (SEQ ID NO. 5), 17015 (SEQ ID NO. 6), 17016 (SEQ ID NO. 7), 17017 (SEQ ID NO. 8), 17019 (SEQ ID NO. 10), 17020 (SEQ ID NO. 11), 17021 (SEQ ID NO. 12), 17022 (SEQ ID NO. 13), 17023 (SEQ ID NO. 14), 17024 (SEQ ID NO. 15), 17025 (SEQ ID NO. 16) 17026 (SEQ ID NO. 17), 17028 (SEQ ID NO. 19), 17029 (SEQ ID NO. 20), and 17030 (SEQ ID NO. 21) resulted in at least 60% inhibition of Fas mRNA expression in this assay. Oligonucleotides 17016 (SEQ ID NO. 7), 17017 (SEQ ID NO. 8), 17019 (SEQ ID NO. 10), 17020 (SEQ ID NO. 11), 17021 (SEQ ID NO. 12), 17022 (SEQ ID NO. 13), 17023 (SEQ ID NO. 14), 17024 (SEQ ID NO. 15), 17025 (SEQ ID NO. 16), and 17026 (SEQ ID NO. 17) resulted in at least 80% inhibition of Fas mRNA expression.

TABLE 1

Nucleotide Sequences of Human Fas Chimeric (deoxy gapped) Phosphorothioate Oligonuleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17012 | CGTAAACCGCTTCCCTCACT | 3 | 0040–0059 | 5'-UTR |
| 17013 | GTGTTCCGTGCCAGTGCCCG | 4 | 0085–0104 | 5'-UTR |
| 17014 | GCCCAGCATGGTTGTTGAGC | 5 | 0210–0229 | AUG |
| 17015 | CTTCCTCAATTCCAATCCCT | 6 | 0318–0337 | coding |
| 17016 | CTTCTTGGCAGGGCACGCAG | 7 | 0463–0482 | coding |
| 17017 | TGCACTTGGTATTCTGGGTC | 8 | 0583–0602 | coding |
| 17018 | GCTGGTGAGTGTGCATTCCT | 9 | 0684–0703 | coding |
| 17019 | CATTGACACCATTCTTTCGA | 10 | 0967–0986 | coding |
| 17020 | TCACTCTAGACCAAGCTTTG | 11 | 1214–1233 | stop |
| 17021 | CCCAGTAAAAAACCAAGCAG | 12 | 1305–1324 | 3'-UTR |
| 17022 | TATGTTGGCTCTTCAGCGCT | 13 | 1343–1362 | 3'-UTR |
| 17023 | ATTTGGGTACTTAGCATGCC | 14 | 1452–1471 | 3'-UTR |
| 17024 | GGGTTAGCCTGTGGATAGAC | 15 | 1568–1587 | 3'-UTR |
| 17025 | CAAAGTGGCCTGCCTGTTCA | 16 | 1641–1660 | 3'-UTR |
| 17026 | TTGAGCCAGTAAAATGCATA | 17 | 1890–1909 | 3'-UTR |
| 17027 | TGAGCACCAAGGCAAAAATG | 18 | 1983–2002 | 3'-UTR |
| 17028 | TCTTGCCTTTTGGTGGACTA | 19 | 2057–2076 | 3'-UTR |
| 17029 | AGCAGTTTTACATGGGACA | 20 | 2222–2241 | 3'-UTR |
| 17030 | GGTATGACAAGAGCAATTCC | 21 | 2291–2310 | 3'-UTR |
| 17031 | GGTGGTTCCAGGTATCTGCT | 22 | 2450–2469 | 3'-UTR |
| 17032 | TATAATTCCAAACACAAGGG | 23 | 2503–2522 | 3'-UTR |

[1]Emboldened residues are 2'-methoxyethoxy residues, 2'-methoxyethoxy cytosine residues are 5-methylcytosines; all linkages are phosphorothioate linkages.
[2]Coordinates from Genbank Accession No. X63717, locus name "HSAPO1", SEQ ID NO. 1.

TABLE 2

Inhibition of Human Fas mRNA expression in C8161 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100.0% | 0.0% |
| 17012 | 3 | 5'-UTR | 98.7% | 1.3% |
| 17013 | 4 | 5'-UTR | 81.3% | 18.7% |
| 17014 | 5 | AUG | 27.1% | 72.9% |
| 17015 | 6 | coding | 30.0% | 70.0% |
| 17016 | 7 | coding | 8.7% | 91.3% |
| 17017 | 8 | coding | 10.1% | 89.9% |
| 17018 | 9 | coding | 186.1% | — |
| 17019 | 10 | coding | 12.9% | 87.1% |
| 17020 | 11 | stop | 7.3% | 92.7% |
| 17021 | 12 | 3'-UTR | 15.8% | 84.2% |
| 17022 | 13 | 3'-UTR | 15.1% | 84.9% |
| 17023 | 14 | 3'-UTR | 11.4% | 88.6% |
| 17024 | 15 | 3'-UTR | 11.3% | 88.7% |
| 17025 | 16 | 3'-UTR | 9.4% | 90.6% |
| 17026 | 17 | 3'-UTR | 19.6% | 80.4% |
| 17027 | 18 | 3'-UTR | 54.3% | 45.7% |
| 17028 | 19 | 3'-UTR | 26.6% | 73.4% |
| 17029 | 20 | 3'-UTR | 23.6% | 76.4% |
| 17030 | 21 | 3'-UTR | 35.5% | 64.5% |
| 17031 | 22 | 3'-UTR | 75.1% | 24.9% |
| 17032 | 23 | 3'-UTR | 58.4% | 41.6% |

The most active oligonucleotide, 17020 (SEQ ID NO. 11) was used in a dose response experiment. C8161 cells were grown and treated as described above except the concentration was varied as shown in Table 3. The LIPOFECTIN® to oligonucleotide ratio was maintained at 3 μg/ml LIPOFECTIN® per 100 nM oligonucleotide. RNA was isolated and quantitated as described above. Included in this experiment were control oligonucleotides with 2, 4, or 6 base mismatches or a scrambled control oligonucleotide. These controls were tested at 300 nM.

Results are shown in Table 3.

TABLE 3

Dose Response of C8161 cells to ISIS 17020

| ISIS # | SEQ ID NO: | ASO Gene Target | Dose | % RNA Expression | % RNA Inhibition |
|---|---|---|---|---|---|
| control | — | — | — | 100% | — |
| 17020 | 11 | stop | 25 nM | 50.6% | 49.4% |
| " | " | " | 50 nM | 44.9% | 55.1% |
| " | " | " | 100 nM | 28.1% | 71.9% |
| " | " | " | 150 nM | 21.8% | 78.2% |
| " | " | " | 200 nM | 24.2% | 75.8% |
| " | " | " | 300 nM | 19.3% | 80.7% |
| " | " | " | 400 nM | 20.6% | 79.4% |

From the dose response curve, oligonucleotide 17020 has an $IC_{50}$ of about 25 nM. Control oligonucleotides with 2, 4, or 6 base mismatches or a scrambled control oligonucleotide showed no inhibition of Fas mRNA expression.

Example 3

Human FasL Oligonucleotide Sequences

Antisense oligonucleotides were designed to target human FasL. Target sequence data are from the Fas ligand cDNA sequence published by Mita, E. et al. (*Biochem. Biophys. Res. Commun.*, 1994, 204, 468–474); Genbank accession number D38122, provided herein as SEQ ID NO: 24. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 4.

NHEK cells, a human epidermal keratinocyte cell line was obtained from Clonetics (Walkersville, Md). NHEK were grown in Keratinocyte Growth Media (KGM) (Gibco BRL, Gaithersburg Md.) containing 5 ng/ml of EGF, bovine pituitary extract. NHEK cells were used at passage 6.

NHEK were grown to 60–80% confluency, washed once with basal media, and then incubated for 4 hours with 5 ml of basal media containing 10 μg/ml LIPOFECTIN® (Gibco BRL, Gaithersburg Md.) and 300 nM of oligonucleotide. The media was replaced with fresh media and cells were incubated for an additonal 20 hours.

Total cellular RNA was isolated by guanidinium isothiocyante extraction followed by ultracentrifugation (see Ausubel, F. M. et al., Current Protocols in Molecular Biology, 1993, John Wiley & Sons, Inc.). Northern blotting was performed as described in Example 2. A FasL probe was generated by PCR using FasL primers (Life Technologies). Signals from Northern blots were quantitated as described in Example 2.

Results are shown in Table 5. Oligonucleotides 16171 (SEQ ID NO. 36), 16172 (SEQ ID NO. 37), 16178 (SEQ ID NO. 43) and 16179 (SEQ ID NO. 44) resulted in at least 45% inhibition of Fas ligand mRNA expression in this assay.

TABLE 4

Nucleotides Sequences of Human FasL Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 16161 | CCATAGCTAAGGGAAACACC | 26 | 0034–0053 | 5'-UTR |
| 16162 | GCCAGCCCCAGCAAACGGTT | 27 | 0152–0171 | 5'-UTR |
| 16163 | TGCATGGCAGCTGGTGAGTC | 28 | 0174–0193 | AUG |
| 16164 | GGAAGAACTGTGCCTGGAGG | 29 | 0261–0280 | coding |
| 16165 | TGGCAGCGGTAGTGGAGGCA | 30 | 0376–0395 | coding |
| 16166 | GCTGTGTGCATCTGGCTGGT | 31 | 0540–0559 | coding |
| 16167 | AATGGGCCACTTTCCTCAGC | 32 | 0614–0633 | coding |
| 16168 | GCAGGTTGTTGCAAGATTGA | 33 | 0785–0804 | coding |
| 16169 | AAGATTGAACACTGCCCCCA | 34 | 0922–0941 | coding |
| 16170 | AATCCCAAAGTGCTTCTCTT | 35 | 1033–1052 | stop |
| 16171 | TTCTCGGTGCCTGTAACAAA | 36 | 1069–1088 | 3'-UTR |
| 16172 | GCTACAGACATTTTGAACCC | 37 | 1169–1188 | 3'-UTR |
| 16173 | CCGTCATATTCCTCCATTTG | 38 | 1220–1239 | 3'-UTR |
| 16174 | CCCTCTTCACATGGCAGCCC | 39 | 1256–1275 | 3'-UTR |
| 16175 | GGTGTCCTTTTCAATCTGCC | 40 | 1338–1357 | 3'-UTR |
| 16176 | CAGTCCCCCTTGAGGTAGCA | 41 | 1385–1404 | 3'-UTR |
| 16177 | GTGAAGATGCTGCCAGTGGG | 42 | 1503–1522 | 3'-UTR |
| 16178 | CCCCTACAATTGGCACTGGA | 43 | 1618–1637 | 3'-UTR |
| 16179 | TCTTGACCAAATGCAACCCA | 44 | 1714–1733 | 3'-UTR |

[1]Emboldened residues are 2'-methoxyethoxy residues, 2'-methoxyethoxy cytosine residues are 5-methyl-cytosines; all linkages are phosphorothioate linkages.
[2]Coordinates from Genbank Accession No. D31822, locus name "HUMHPC", SEQ ID NO. 24.

TABLE 5

Inhibition of Human FasL mRNA expression in NHEK Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100.0% | 0.0% |
| 16161 | 26 | 5'-UTR | 127.0% | — |
| 16162 | 27 | 5'-UTR | 136.0% | — |
| 16163 | 28 | AUG | 119.0% | — |
| 16164 | 29 | coding | 110.0% | — |
| 16165 | 30 | coding | 124.0% | — |
| 16166 | 31 | coding | 131.0% | — |
| 16167 | 32 | coding | 142.0% | — |
| 16168 | 33 | coding | 137.0% | — |
| 16169 | 34 | coding | 111.0% | — |
| 16170 | 35 | stop | 108.0% | — |
| 16171 | 36 | 3'-UTR | 53.0% | 47.0% |
| 16172 | 37 | 3'-UTR | 50.0% | 50.0% |
| 16173 | 38 | 3'-UTR | 91.0% | 9.0% |
| 16174 | 39 | 3'-UTR | 136.0% | — |
| 16175 | 40 | 3'-UTR | 69.0% | 31.0% |
| 16176 | 41 | 3'-UTR | 130.0% | — |
| 16177 | 42 | 3'-UTR | 94.0% | 6.0% |
| 16178 | 43 | 3'-UTR | 55.0% | 45.0% |
| 16179 | 44 | 3'-UTR | 48.0% | 52.0% |

Example 4

Human Fap-1 Oligonucleotide Sequences

Antisense oligonucleotides were designed to target human Fap-1. Target sequence data are from the protein tyrosine phosphatase (PTP-BAS, type 1) cDNA sequence published by Maekawa, K. et al. (*FEBS Lett.*, 1994, 337, 200–206); Genbank accession number D21209, provided herein as SEQ ID NO: 45. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines and 2'-deoxy cytosines were 5-methyl-cytosines. These oligonucleotide sequences are shown in Table 6.

C8161 cells were grown and treated with oligonucleotide as described in Example 2 except that 9 μg/ml LIPOFECTIN® was used. mRNA was isolated and quantitated as described in Example 2.

Results are shown in Table 7. Oligonucleotides 16148 (SEQ ID NO. 48), 18470 (SEQ ID NO. 50), 18471 (SEQ ID NO. 51), 18472 (SEQ ID NO. 52), 18473 (SEQ ID NO. 53), 18479 (SEQ ID NO. 58), 18480 (SEQ ID NO. 59), 18481 (SEQ ID NO. 60), and 18485 (SEQ ID NO. 64) resulted in greater than 60% inhibition of Fap-1 mRNA expression in this assay. Oligonucleotide 18479 (SEQ ID NO. 58) resulted in greater than 85% inhibition.

TABLE 6

Nucleotide Sequences of Human FAP-1 Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 18467 | ACGTGCATATTACCGGCTGG | 47 | 0052–0071 | AUG |
| 18468 | GAGAAATGATGAAGCCAAGG | 48 | 0201–0220 | coding |
| 18469 | GTTGGCTCTGAGGCACTTCA | 49 | 0405–0424 | coding |
| 18470 | TTTGTCTCTCTCGGATTCGG | 50 | 1200–1219 | coding |
| 18471 | GCCAAAGAAATTCCTCAGTT | 51 | 1664–1683 | coding |
| 18472 | AAGGATGCCAGCAATAAGGA | 52 | 2158–2177 | coding |
| 18473 | GGTCTTCAATGGATGAGGAG | 53 | 3189–3208 | coding |
| 18474 | GTGGTGATCCTTGGAAGAAG | 54 | 3701–3720 | coding |
| 18475 | TCCACTCCCACTGCTGTCAC | 55 | 5021–5040 | coding |
| 18476 | TTCTCTGATTGCCTTTGGTT | 56 | 5472–5491 | coding |
| 18478 | GCAACTCATCATTTCCCCAT | 57 | 6513–6532 | coding |
| 18479 | CCAGAGGCTTTTTCATGTC | 58 | 7520–7539 | stop |
| 18480 | GCATCCAGAGGCTCTTTTCA | 59 | 7524–7543 | 3'-UTR |
| 18481 | GCTGGAGGTTAAGGAGAGAA | 60 | 7552–7571 | 3'-UTR |
| 18482 | TTTGGATAGAGAGCAGGAGT | 61 | 7574–7593 | 3'-UTR |
| 18483 | TTTCAAGAAGAATACCCCTA | 62 | 7648–7667 | 3'-UTR |
| 18484 | GCTGCCTTTAATCATCCCTA | 63 | 7760–7779 | 3'-UTR |
| 18485 | ACTGGTTTCAAGTATCCCCT | 64 | 7891–7910 | 3'-UTR |

[1]Emboldened residues are 2'-methoxyethoxy residues, 2'-methoxyethoxy cytosine residues and 2'-OH cytosine residues are 5-methyl-cytosines; all linkages are phosphorothioate linkages.
[2]Coordinates from Genbank Accession No. D21209, locus name "HUMPTPB1", SEQ ID NO. 45.

TABLE 7

Inhibition of Human Fap-1 mRNA expression in C8161 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100.0% | 0.0% |
| 18468 | 48 | coding | 33.4% | 66.6% |
| 18469 | 49 | coding | 71.9% | 28.1% |
| 18470 | 50 | coding | 33.2% | 66.8% |
| 18471 | 51 | coding | 33.3% | 66.7% |
| 18472 | 52 | coding | 26.9% | 73.1% |
| 18473 | 53 | coding | 28.3% | 71.7% |
| 18474 | 54 | coding | 51.9% | 48.1% |
| 18475 | 55 | coding | 46.2% | 53.8% |
| 18476 | 56 | coding | 133.6% | — |
| 18479 | 57 | stop | 11.6% | 88.4% |
| 18480 | 59 | 3'-UTR | 30.8% | 69.2% |
| 18481 | 60 | 3'-UTR | 35.2% | 64.8% |
| 18482 | 61 | 3'-UTR | 55.0% | 45.0% |
| 18483 | 62 | 3'-UTR | 55.3% | 44.7% |
| 18485 | 64 | 3'-UTR | 35.6% | 64.4% |

Example 5
Mouse Fas Oligonucleotide Sequences

Antisense oligonucleotides were designed to target mouse Fas. Target sequence data are from the Fas cDNA sequence published by Watanabe-Fukunaga, R. et al. (*J. Immunol.*, 1992, 148, 1274–1297); Genbank accession number M83649, provided herein as SEQ ID NO: 65. Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE and 2'-OH cytosines were 5-methyl-cytosines. Oligonucleotide sequences are shown in Table 8.

AML12 cells, a murine hepatocyte cell line, was obtained from ATCC (Manassas, Va.). AML12 cells were cultured in a 1:1 mixture of DMEM and F12 medium with 5.0 µg/ml insulin, 5.0 µg/ml transferrin, 5.0 ng/ml selenium, 0.04 µg/ml dexamethasone and 10% FBS (all cell culture reagents available from Life Technologies).

AML12 cells were transfected with oligonucleotides as described in Example 2 for C8161 cells except oligonucleotide treatment was for six hours. For an initial screen, AML12 cells were transfected with 300 nM oligonucleotide and RNA collected 24 hours later.

Total cellular RNA was isolated using the RNEASY® kit (Qiagen, Santa Clarita, Calif.). RNAse protection experiments were conducted using RIBOQUANT™ kits and the mAPO-2 Custom Probe Set set according to the manufacturer's instructions (Pharmingen, San Diego, Calif.). mRNA levels were quantitated using a PhosphorImager (Molecular Dynamics, Sunnyvale, Calif.).

Results are shown in Table 9. Oligonucleotides 22017 (SEQ ID NO. 67), 22018 (SEQ ID NO. 68), 22019 (SEQ ID NO. 69), 22023 (SEQ ID NO. 73), 22024 (SEQ ID NO. 74), 22025 (SEQ ID NO. 75), 22026 (SEQ ID NO. 76), 22027 (SEQ ID NO. 77), 22028 (SEQ ID NO. 78), 22030 (SEQ ID NO. 80) and 22032 (SEQ ID NO. 82) gave better than 40% inhibition of Fas mRNA in this assay. Oligonucleotides 22018 (SEQ ID NO. 68), 22023 (SEQ ID NO. 73), 22026 (SEQ ID NO. 76), 22028 (SEQ ID NO. 78), and 22030 (SEQ ID NO. 80) gave better than 60% inhibition of Fas mRNA.

TABLE 8

Nucleotide Sequences of Mouse Fas Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22017 | GCAGCAAGGGAAAACAGCGG | 67 | 0026–0045 | 5'-UTR |
| 22018 | CCACAGCATGTCTGCAGCAA | 68 | 0039–0058 | AUG |
| 22019 | TTTCATGAACCCGCCTCCTC | 69 | 0148–0167 | coding |
| 22020 | GGGTCAGGGTGCAGTTTGTT | 70 | 0385–0404 | coding |
| 22021 | GAGGCGCAGCGAACACAGTG | 71 | 0461–0480 | coding |
| 22022 | CATAGGCGATTTCTGGGACT | 72 | 0542–0561 | coding |
| 22023 | TCCAGCACTTTCTTTTCCGG | 73 | 0616–0635 | coding |
| 22024 | GGTTTCACGACTGGAGGTTC | 74 | 0663–0682 | coding |
| 22025 | CTTCAGCAATTCTCGGGATG | 75 | 0721–0740 | coding |
| 22026 | GCCCTCCTTGATGTTATTTT | 76 | 0777–0796 | coding |
| 22027 | GGTACCAGCACAGGAGCAGC | 77 | 0583–0872 | coding |
| 22028 | CGGCTTTTTGCGCACCCTTG | 78 | 0910–0929 | coding |
| 22029 | GTGTCTGGGGTTGATTTTCC | 79 | 0980–0999 | coding |
| 22030 | TCTCCTCTCTTCATGGCTGG | 80 | 1048–1067 | 3'-UTR |
| 22031 | GGCATTCATTTTGTTTCCAT | 81 | 1840–1103 | 3'-UTR |
| 22032 | TCCCTGGAACCTGCTAGTCA | 82 | 1180–1199 | 3'-UTR |
| 22033 | TCAGCAACTGCAGAGAATAA | 83 | 1209–1228 | 3'-UTR |
| 22034 | GCAGATTCCACTTCACATTT | 84 | 1290–1309 | 3'-UTR |
| 22035 | AAGGTCTTCAATTAACTGCG | 85 | 1372–1391 | 3'-UTR |

[1]Emboldened residues are 3'-methoxyethoxy residues, 2'-methoxyethoxy cytosine residues and 2'-OH cytosine residues are 5-methyl-cytosines; all linkages are phosphorothioate linkages.
[2]Coordinates from Genbank Accession No. M83649, locus name "MUSFASANT", SEQ ID NO. 65.

TABLE 9

Inhibition of Mouse Fas mRNA expression in AML12 Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| LIPOFECTIN ® | — | — | 136% | — |
| 22017 | 67 | 5'-UTR | 44% | 56% |
| 22018 | 68 | AUG | 38% | 62% |
| 22019 | 69 | coding | 56% | 44% |
| 22020 | 70 | coding | 69% | 31% |
| 22021 | 71 | coding | 77% | 23% |
| 22022 | 72 | coding | 77% | 23% |
| 22023 | 73 | coding | 37% | 63% |
| 22024 | 74 | coding | 49% | 51% |
| 22025 | 75 | coding | 57% | 43% |
| 22026 | 76 | coding | 31% | 69% |
| 22027 | 77 | coding | 53% | 47% |
| 22028 | 78 | coding | 28% | 72% |
| 22029 | 79 | coding | 82% | 18% |
| 22030 | 80 | 3'-UTR | 22% | 78% |
| 22031 | 81 | 3'-UTR | 76% | 24% |
| 22032 | 82 | 3'-UTR | 47% | 53% |
| 22033 | 83 | 3'-UTR | 103% | — |
| 22034 | 84 | 3'-UTR | 80% | 20% |
| 22035 | 85 | 3'-UTR | 98% | 2% |

Example 6

Dose Response of Antisense Chimeric (Deoxy Gapped) Phosphorothioate Oligonucleotide Effects on Mouse Fas mRNA Levels in AML12 Cells Oligonucleotides 22019 (SEQ ID. NO. 69), 22023 (SEQ ID. NO. 73) and 22028 (SEQ ID. NO. 78) was chosen for a dose response study. AML12 cells were grown, treated and processed as described in Example 5.

Results are shown in Table 10. $IC_{50}$s were 150 nM or less and maximal inhibition seen was greater than 80%.

TABLE 10

Dose Response of AML12 cells to Fas Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | — |
| 22019 | 69 | coding | 75 nM | 60% | 40% |
| " | " | " | 150 nM | 53% | 47% |
| " | " | " | 300 nM | 34% | 66% |
| " | " | " | 500 nM | 14% | 86% |
| 22023 | 73 | coding | 75 nM | 61% | 39% |
| " | " | " | 150 nM | 28% | 72% |
| " | " | " | 300 nM | 22% | 78% |
| " | " | " | 500 nM | 20% | 80% |
| 22028 | 78 | coding | 75 nM | 57% | 43% |
| " | " | " | 150 nM | 49% | 51% |
| " | " | " | 300 nM | 42% | 58% |
| " | " | " | 500 nM | 45% | 55% |

A similar experiment was performed which included mismatch control oligonucleotides (2, 4, 6 or 8 base mismatches). None of these control oligonucleotides inhibited Fas mRNA expression.

Example 7

Inhibition of Fas Expression in Balb/c Mice by Fas Antisense Chimeric (Deoxy Gapped) Phosphorothioate Oligonucleotides Balb/c mice were used to assess the activity of Fas antisense oligonucleotides. Female Balb/c mice, 8 to 10 weeks old, were intraperitoneally injected with oligonucleotide at 100 mg/kg mouse body weight. Mice were injected daily for four days. Control mice were injected with a saline solution. After the fourth day, the livers were removed from the animals and analyzed for Fas mRNA expression. RNA was extracted using the RNEASY® kit (Qiagen, Santa Clarita, Calif.) and quantitated using RPA as described in Example 5.

Results are shown in Table 11. Maximal inhibition seen in this assay was 80%.

TABLE 11

Inhibition of Mouse Fas mRNA expression in Balb/c Mice by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 22019 | 69 | coding | 40% | 60% |
| 22023 | 73 | coding | 20% | 80% |
| 22028 | 78 | coding | 21% | 79% |

A dose response experiment was performed in Balb/c mice using oligonucleotides 22023 (SEQ ID NO. 73) and 22028 (SEQ ID NO. 78). Mice were treated as described above except the concentration of oligonucleotide was varied as shown in Table 12. Results are shown in Table 12. $IC_{50}$s for these oligonucleotides is estimated to be about 9 mg/kg. Maximal inhibition seen was greater than 90%.

TABLE 12

Dose Response of Balb/c to Fas Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | — |
| 22023 | 73 | coding | 6 mg/kg | 66% | 34% |
| " | " | " | 12 mg/kg | 40% | 60% |
| " | " | " | 25 mg/kg | 26% | 74% |
| " | " | " | 50 mg/kg | 8% | 92% |
| " | " | " | 100 mg/kg | 6% | 94% |
| 22028 | 78 | coding | 6 mg/kg | 65% | 35% |
| " | " | " | 12 mg/kg | 40% | 60% |
| " | " | " | 25 mg/kg | 17% | 83% |
| " | " | " | 50 mg/kg | 12% | 88% |
| " | " | " | 100 mg/kg | 13% | 87% |

Oligonucleotide 22023 (SEQ ID NO. 73) was chosen for a time course study. Balb/c mice were treated as described above except that doses of 6 mg/kg and 12 mg/kg were used and treatment time (in days) was varied as shown in Table 13.

Results are shown in Table 13. Increasing the treatment time, in general, gave better results.

TABLE 13

Time Course of Balb/c to Fas Chimeric (deoxy gapped) Phosphorothioate Oligonucleotide

| ISIS # | SEQ ID NO: | ASO Gene Target | Dose | Treatment Time | % mRNA Inhibition |
|---|---|---|---|---|---|
| control | — | — | — | — | — |
| 22023 | 73 | coding | 6 mg/kg | 2 d | 54% |
| " | " | " | " | 4 d | 55% |

TABLE 13-continued

Time Course of Balb/c to Fas
Chimeric (deoxy gapped) Phosphorothioate Oligonucleotide

| ISIS # | SEQ ID NO: | ASO Gene Target | Dose | Treatment Time | % mRNA Inhibition |
|---|---|---|---|---|---|
| " | " | " | " | 7 d | 84% |
| " | " | " | " | 12 d | 87% |
| 22023 | 73 | coding | 12 mg/kg | 2 d | 40% |
| " | " | " | " | 4 d | 79% |
| " | " | " | " | 7 d | 92% |
| " | " | " | " | 12 d | 82% |

The effect of oligonucleotides 22023 (SEQ ID NO. 69) and 22028 (SEQ ID NO. 78) on Fas protein expression was examined. Balb/c mice were injected with oligonucleotide as described above. Lpr mice (Jackson Laboratory, Bar Harbor, Me.), a Fas knockout strain, were used as a control. Four hours after the last dose, the mice were sacrificed and a piece of liver was frozen in O.C.T. compound (Sakura Finetek U.S.A., Inc., Torrance, Calif.). The liver was fixed for 1 minute in acetone, then stained with Fas antibody (rabbit anti rat/mouse fas, Research Diagnostics, Inc., Flanders, N.J.) at 0.7 µg/ml for 45 minutes. A second antibody (HRP conjugated donkey anti-rabbit, Jackson Laboratory) was then added at 1:100 dilution for 30 minutes. Then DAB (DAKO Corporation, Carpinteria, Calif.) was added for color development. Tissue sections were visualized under a microscope.

Treatment with Fas antisense oligonucleotides reduced Fas protein expression to levels similar to those in Lpr mice.

Example 8

Effect of Fas Antisense Oligonucleotides in a Con A Murine Model for Hepatitis

Concanavalin A-induced hepatitis is used as a murine model for autoimmune hepatitis (Mizuhara, H., et al., *J. Exp. Med.*, 1994, 179, 1529–1537). It has been shown that this type of liver injury is mediated by Fas (Seino, K., et al., *Gastroenterology* 1997, 113, 1315–1322). Certain types of viral hepatitis, including Hepatitis C, are also mediated by Fas (*J. Gastroenterology and Hepatology*, 1997, 12, S223–S226). Female Balb/c between the ages of 6 weeks and 3 months were used to assess the activity of Fas antisense oligonucleotides.

For determining the effect of Fas antisense oligonucleotides on Fas mRNA expression, mice were injected intraperitoneally with oligonucleotide 22023 (SEQ ID NO. 73) at 50 mg/kg or 100 mg/kg, daily for 4 days. The pretreated mice were then intravenously injected with 0.3 mg concanavalin A (Con A) to induce liver injury. Within 24 hours following Con A injection, the livers were removed from the animals and RNA isolated using the RNEASY® kit (Qiagen, Santa Clarita, Calif.) and quantitated using RPA as described in Example 5.

Results are shown in Table 14.

TABLE 14

Reduction of Balb/c Liver Fas mRNA with Fas
Antisense Chimeric (deoxy gapped) Phosphorothioate
Oligonucleotide following ConA treatment

| ISIS # | SEQ ID NO: | ASO Gene Target | Dose | % mRNA Expression | % mRNA Inhibition |
|---|---|---|---|---|---|
| control | — | — | — | 100% | — |
| 22023 | 73 | coding | 50 mg/kg | 16% | 84% |
| " | " | " | 100 mg/kg | 18% | 82% |

Example 9

Effect of Fas Antisense Oligonucleotides in a Fas Cross-linking Antibody Murine Model for Hepatitis Injection of agonistic Fas-specific antibody into mice can induce massive hepatocyte apoptosis and liver hemorrhage, and death from acute hepatic failure (Ogasawara, J., et al., *Nature*, 1993, 364, 806–809). Apoptosis-mediated aberrant cell death has been shown to play an important role in a number of human diseases. For example, in hepatitis, Fas and Fas ligand up-regulated expression are correlated with liver damage and apoptosis. It is thought that apoptosis in the livers of patients with fulminant hepatitis, acute and chronic viral hepatitis, autoimmune hepatitis, as well as chemical or drug induced liver intoxication may result from Fas activation on hepatocytes.

8–10 week old female Balb/c mice were intraperitoneally injected with oligonucleotides 22023 (SEQ ID NO. 73) and 22028 (SEQ ID NO. 78) at 50 mg/kg, daily for 4 days. Four hours after the last dose, 7.5 µg of mouse Fas antibody (Pharmingen, San Diego, Calif.) was injected into the mice. Mortality of the mice was measured for more than 10 days following antibody treatment.

Results are shown in Table 15. Mortality is expressed as a fraction where the denominator is the total number of mice used and the numerator is the number that died.

TABLE 15

Protective Effects of Fas Antisense Chimeric
(deoxy gapped) Phosphorothioate Oligonucleotides in Fas
Antibody Cross-linking Induced Death in Balb/c Mice

| ISIS # | SEQ ID NO: | ASO Gene Target | Dose | Mortality |
|---|---|---|---|---|
| saline | — | — | — | 6/6 |
| 22023 | 73 | coding | 50 mg/kg | 0/6 |
| 22028 | 78 | coding | 50 mg/kg | 0/6 |

Oligonucleotides 22023 (SEQ ID NO. 73) and 22028 (SEQ ID NO. 78) completely protected the Fas antibody treated mice from death. Mice injected with saline or scrambled control oligonucleotide did not confer any protective effect.

Total RNA was extracted from the livers of Fas antibody treated mice using the RNEASY® kit (Qiagen, Santa Clarita, Calif.). Fas mRNA expression was quantitated using RPA as described in Example 5. It was found that high levels of Fas mRNA expression in this model correlated with increased mortality of Fas antibody treated mice.

What is claimed is:

1. An antisense compound up to 30 nucleobases in length targeted to a nucleic acid molecule encoding Fas, wherein said antisense compound specifically hybridizes with said nucleic acid molecule and inhibits the expression of Fas and wherein said antisense compound has a sequence comprising at least an 8 nucleobase portion of SEQ ID NO: 11, 12, 14, 15, 16, 17, 19, 20, or 21.

2. The antisense compound of claim 1 which is an antisense oligonucleotide.

3. The antisense compound of claim 2 wherein the antisense oligonucleotide comprises at least one modified internucleoside linkage.

4. The antisense compound of claim 3 wherein the modified internucleoside linkage is a phosphorothioate linkage.

5. The antisense compound of claim 2 wherein the antisense oligonucleotide comprises at least one modified sugar moiety.

6. The antisense compound of claim 5 wherein the modified sugar moiety is a 2'-O-methoxyethyl moiety.

7. The antisense compound of claim 2 wherein the antisense oligonucleotide comprises at least one modified nucleobase.

8. The antisense compound of claim 7 wherein modified nucleobase is a 5-methyl cytosine.

9. The antisense compound of claim 2 wherein the antisense oligonucleotide is a chimeric oligonucleotide.

10. A composition comprising the antisense compound of claim 1 and a pharmaceutically acceptable carrier or diluent.

11. The composition of claim 10 further comprising a colloidal dispersion system.

12. The composition of claim 10 wherein the antisense compound is an antisense oligonucleotide.

13. A method of inhibiting the expression of Fas in cells or tissues comprising contacting said cells or tissues in vitro with the antisense compound of claim 1 so that expression of Fas is inhibited.

14. An antisense compound 8 to 30 nucleobases in length targeted to the coding region of a nucleic acid molecule encoding Fas, wherein said antisense compound inhibits the expression of said Fas and has a sequence comprising SEQ ID NO: 6, 7, 8, or 10.

15. The antisense compound of claim 14 which is an antisense oligonucleotide.

16. The antisense compound of claim 15 wherein the antisense oligonucleotide comprises at least one modified internucleoside linkage.

17. The antisense compound of claim 16 wherein the modified internucleoside linkage is a phosphorothioate linkage.

18. The antisense compound of claim 15 wherein the antisense oligonucleotide comprises at least one modified sugar moiety.

19. The antisense compound of claim 18 wherein the modified sugar moiety is a 2'-O-methoxyethyl moiety.

20. The antisense compound of claim 15 wherein the antisense oligonucleotide comprises at least one modified nucleobase.

21. The antisense compound of claim 20 wherein modified nucleobase is a 5-methyl cytosine.

22. The antisense compound of claim 15 wherein the antisense oligonucleotide is a chimeric oligonucleotide.

23. A composition comprising the antisense compound of claim 14 and a pharmaceutically acceptable carrier or diluent.

24. The composition of claim 23 further comprising a colloidal dispersion system.

25. The composition of claim 23 wherein the antisense compound is an antisense oligonucleotide.

26. A method of inhibiting the expression of Fas in cells or tissues comprising contacting said cells or tissues in vitro with the antisense compound of claim 14 so that expression of Fas is inhibited.

27. An antisense compound targeted to a nucleic acid molecule encoding Fas, wherein said antisense compound specifically hybridizes with said nucleic acid molecule and inhibits the expression of Fas and wherein said antisense compound has a sequence consisting of SEQ ID NO: 5 or 13.

28. The antisense compound of claim 27 which is an antisense oligonucleotide.

29. The antisense compound of claim 28 wherein the the antisense oligonucleotide comprises at least one modified internucleoside linkage.

30. The antisense compound of claim 29 wherein the modified internucleoside linkage is a phosphorothioate linkage.

31. The antisense compound of claim 28 wherein the antisense oligonucleotide comprises at least one modified sugar moiety.

32. The antisense compound of claim 31 wherein the modified sugar moiety is a 2'-O-methoxyethyl sugar moiety.

33. The antisense compound of claim 28 wherein the the antisense oligonucleotide comprises at least one modified nucleobase.

34. The antisense compound of claim 33 wherein the modified nucleobase is a 5-methylcytosine.

35. The antisense compound of claim 28 wherein the antisense oligonucleotide is a chimeric oligonucleotide.

36. A composition comprising the antisense compound of claim 27 and a pharmaceutically acceptable carrier or diluent.

37. The composition of claim 36 further comprising a colloidal dispersion system.

38. The composition of claim 36 wherein the antisense compound is an antisense oligonucleotide.

39. A method of inhibiting the expression of Fas in cells or tissues comprising contacting said cells or tissues in vitro with the antisense compound of claim 27 so that expression of Fas is inhibited.

* * * * *